(12) United States Patent
Mohanakumar

(10) Patent No.: US 12,276,669 B2
(45) Date of Patent: Apr. 15, 2025

(54) SYSTEMS AND METHODS FOR DIAGNOSING AND TREATING CHRONIC ORGAN REJECTION

(71) Applicant: Dignity Health, San Francisco, CA (US)

(72) Inventor: Thalachallour Mohanakumar, Phoenix, AZ (US)

(73) Assignee: Dignity Health, San Francisco, CA (US)

( * ) Notice: Subject to any disclaimer, the term of this patent is extended or adjusted under 35 U.S.C. 154(b) by 792 days.

(21) Appl. No.: 16/856,418

(22) Filed: Apr. 23, 2020

(65) Prior Publication Data

US 2020/0348317 A1 Nov. 5, 2020

Related U.S. Application Data

(60) Provisional application No. 62/841,076, filed on Apr. 30, 2019.

(51) Int. Cl.
*A61K 9/12* (2006.01)
*G01N 33/68* (2006.01)

(52) U.S. Cl.
CPC ........... *G01N 33/6893* (2013.01); *A61K 9/12* (2013.01); *G01N 2333/78* (2013.01); *G01N 2800/245* (2013.01)

(58) Field of Classification Search
CPC . G01N 33/6893; G01N 2800/245; A61K 9/12
See application file for complete search history.

(56) References Cited

PUBLICATIONS

Hachem et al., American Journal of Transplantation 2012;12:2164-2171 (Year: 2012).*
Parekh et al., Transplantation Proceedings, 2004;36 (Suppl 2S):318S-322S (Year: 2004).*
Mohanakumar et al., Journal of Heart and Lung Transplantation, vol. 37, No. 4S, Apr. 2018, 62 (Year: 2018).*
Gregson et al. "Altered Exosomal RNA Profiles in Bronchoalveolar Lavage from Lung Transplants with Acute Rejection," American Journal of Respiratory and Critical Care Medicine vol. 192 No. 12 Dec. 2015.
Gunasekaran et al. "Circulating Exosomes with Distinct Properties during Chronic Lung Allograft Rejection," The Journal of Immunology 200: 2535-2541 Apr. 2018.
Hwang et al. "Exosome-Allorecognition in Lung Transplantation Rejection," Immunology Research and Therapy Journal 2018; 1(1): 114.

(Continued)

*Primary Examiner* — San Ming R Hui
(74) *Attorney, Agent, or Firm* — Polsinelli PC

(57) ABSTRACT

Embodiments of the invention provide a method for diagnosing and treating chronic organ rejection in a subject that has previously received an allographic organ transplant. The method may include (i) receiving a sample from the subject, wherein the subject does not yet experience symptoms of chronic organ rejection and (ii) measuring expression of at least one marker within the sample. In some aspects, the method may also include (iii) treating the subject with at least one therapeutic methodology when the expression of the at least one marker is increased compared to expression of the marker in a control sample.

10 Claims, 15 Drawing Sheets

(56) References Cited

PUBLICATIONS

Gunasekaran et al. "Donor-Derived Exosomes with Lung Self-Antigens in Human Lung Allograft Rejection," American Journal of Transplantation, 2017; 17: 474-484.

Perez-Hernandez et al. "Donor-derived exosomes: key in lung allograft rejection?," Annals of Translational Medicine 2017;5(4):85.

Sharma et al. "Tissue-associated self-antigens containing exosomes: Role in allograft rejection," Human Immunology Sep. 2018 ; 79(9): 653-658.

Vallabhajosyula et al. "Tissue-Specific Exosome Biomarkers for noninvasively monitoring immunologic rejection pf transplanted tissue," Journal of Clinical Investigations vol. 127, No. 4 Apr. 2017 1375-1391.

Gunasekaran et al. "Exosomes with Lung Associated Self-Antigens (Collagen V and K alpha 1 Tubulin): Role in Rejection Following Human Lung Transplantation," Meeting Abstract: 2016 American Transplant Congress Jun. 12, 2016.

* cited by examiner

SYSTEMS AND METHODS FOR DIAGNOSING AND TREATING CHRONIC ORGAN REJECTION

CROSS REFERENCE TO RELATED APPLICATION

This application claims priority, under 35 U.S.C. § 119(e), to U.S. Provisional Patent Application Ser. No. 62/841,076, filed Apr. 30, 2019. The contents the provisional application are herein incorporated by reference in their entirety for any purposes.

STATEMENT REGARDING FEDERALLY SPONSORED RESEARCH

The present subject matter was made with government support under AI123034 awarded by the National Institutes of Health. The government has certain rights in the present subject matter.

FIELD OF THE INVENTION

The present invention is generally related to systems and methods for diagnosing and/or treating chronic organ rejection, and particularly related to systems and methods for diagnosing and treating chronic organ rejection, such as bronchiolitis obliterans syndrome, via the analysis of self-antigens.

BACKGROUND OF THE INVENTION

The development of chronic rejection following solid organ transplantation is a major barrier for continued function of the transplanted organ. It is recognized that once chronic rejection develops, there are no treatment options currently available to reverse the process. Among various transplanted organs, chronic rejection is most common following human lung transplantation (LTx), where the five year incidence of chronic rejection is approximately 50% and nearly 90% of recipients develop chronic rejection within 10 years of transplantation. Lung allograft failure, due to chronic lung allograft dysfunction, is the leading cause of death beyond the first year after transplantation. Approximately 70% of patients with chronic lung allograft dysfunction have bronchiolitis obliterans syndrome (BOS) with histologic features of obliterative bronchiolitis, a fibrotic obliteration of respiratory and membranous bronchioles. Histologic confirmation of obliterative bronchiolitis is often difficult because surgical lung biopsy is invasive and carries unacceptable risk. In addition, the sensitivity of transbronchial lung biopsy is poor because of the limited sample size and the patchy involvement of respiratory and membranous bronchioles. Therefore, BOS, diagnosed and staged according to changes in spirometry, was developed as the clinical surrogate for obliterative bronchiolitis. Nonetheless, it is recognized that changes in spirometry are downstream of the underlying pathogenic injury that results in the characteristic small airway fibrosis. Although a decrement in small airway forced expiratory flow ($FEF_{25-75}\%$) may presage the decrement in forced expiratory volume ($FEV_1$), this lacks specificity for BOS. Previous studies have demonstrated Broncho alveolar lavage fluid and its cells transcriptome may serves as biomarker in diagnose of BOS.

Thus, there is a clinical need for a biomarker assay that predicts the development of BOS at an early stage to enhance monitoring and provide an opportunity for early intervention.

SUMMARY OF THE INVENTION

Some embodiments may provide systems and methods of diagnosing and/or treating chronic organ rejection. For example, in some aspects, the organs may comprise solid organs, such as lungs, hearts, kidneys, etc. In other aspects, the organs may comprise non-solid organs, such a bone marrow.

In some embodiments, the method may include monitoring a subject that has previously received an allographic organ transplant (i.e., an organ transplant from another subject that is substantially unrelated to the subject). In some aspects, the subject may not yet be showing any outward symptoms of chronic organ rejection. In some embodiments, the method may include receiving a sample from the subject (e.g., a subject who is not yet showing any outward symptoms of chronic organ rejection) and then measuring the expression of at least one marker within the sample. In some aspects, the at least one marker may comprise one or more markers on the surface of one or more biological units disposed within the subject's sample. For example, the one or more markers may be disposed on the surface of, within, other otherwise associated with, one or more exosomes.

In some aspects, the at least one marker may comprise a plurality of markers, such as two markers. Moreover, in some aspects, the markers may comprise one or more self-antigens. For example, in some aspects, the markers may comprise K-alpha 1 tubulin and Collagen-V. In other embodiments, the markers may comprise any other self-antigens. For example, in some aspects, the self-antigens may comprise self-antigens generally associated with heart transplants (e.g., myosin and vimentin) and/or kidney transplants (e.g., fibronectin, Collagen-IV, and/or perlecan/LG3).

Some embodiments may additionally include treating the subject with at least one therapeutic methodology when the expression of the at least one marker is increased compared to expression of the marker in a control sample. For example, when a lung transplant-related antigen is found to be in the subject's sample (e.g., in exosomes found in the sample) at greater levels compared to control levels, then a treatment methodology can be employed. For example, in some aspects, the treatment may comprise an increase in the amount, number, or concentration of immunosuppressants administered to the patient. Specifically, some or all subjects that have received an allographic organ transplant receive immunosuppressants to control potential rejection of the transplanted organ. As such, after detection of the increased expression of the marker in the subject's sample, the subject may be placed on an increased dose or increased number of doses of an immunosuppressant that they were previously receiving. In some aspects, after detection of an increased level of a marker in the subject's sample, the subject may also receive different and/or additional immunosuppressants. For example, the subject may receive cyclosporine, tacrolimus, mycophenolate mofetil, sirolimus, azathioprine, alemtuzumab, and one or more statins. Moreover, in some aspects, the therapeutic methodology may comprise a retransplantation of the organ(s) that was/were previously transplanted from a donor.

Some embodiments of the invention may provide a method of detecting and treating bronchiolitis obliterans syndrome (BOS) in a subject, the subject having previously received an allographic lung transplant (e.g., a single or a bilateral lung transplant). In some aspects, the method may include initially receiving a liquid sample from the subject. In some embodiments, the liquid sample may comprise a blood or a plasma sample from the subject.

In some aspects, the subject may not yet be demonstrating any discernable symptoms of BOS. Moreover, in some embodiments, the method may also include isolating exosomes from the liquid sample and thereafter measuring expression levels of at least one marker within the exosomes. For example, the at least one marker may comprise one or both of Collagen-V and K-alpha 1 tubulin.

Some embodiments may additionally include treating the subject with at least one therapeutic methodology when the expression of the at least one marker is increased compared to expression of the marker in a control sample. For example, when a lung transplant-related self-antigen is found to be in the subject's sample (e.g., in exosomes found in the sample) at greater levels compared to control levels, then a treatment methodology can be employed. For example, in some aspects, the treatment may comprise an increase in the amount, number, or concentration of immunosuppressants administered to the patient. Specifically, some or all subjects that have received an allographic organ transplant receive immunosuppressants to control potential rejection of the transplanted organ. As such, after detection of the increased expression of the marker in the subject's sample, the subject may be placed on an increased dose or increased number of doses of an immunosuppressant that they were previously receiving. In some aspects, after detection of an increased level of a marker in the subject's sample, the subject may also receive different and/or additional immunosuppressants. For example, the subject may receive cyclosporine, tacrolimus, mycophenolate mofetil, sirolimus, azathioprine, alemtuzumab, and one or more statins. Moreover, in some aspects, the therapeutic methodology may comprise a retransplantation of the single or bilateral lung transplant.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

(FIG. 1A) Exosomes were isolated by ultracentrifugation and/or kit method, diluted in PBS and subjected to NanosightNS300 analysis and results showed the extracellular vesicles has size of 60-200 nM. (FIG. 1B) Western blot analysis showed presence of exosomes markers CD9, Alix in exosomes isolated from plasma of stable and bronchiolitis obliterans syndrome (BOS) patients. (FIG. 1C) Exosomes contain Collagen V (Col-V) and Kα1 Tubulin (Kα1T) isolated from plasma collected at the time of BOS diagnosis: Exosomes were isolated from plasma of lung transplant recipients (LTxRs) at a different collaborating center diagnosed with BOS (n=10) and stable (time match control) (n=10) and subjected to western blot analysis for the detection of self-antigens. Western blot analysis showed: increased amount of Col-V and Kα1T in exosomes derived from BOS LTxRs but not in stable. Representation depicts 5 out of 10 LTxRs from BOS (top) and stable (bottom). (FIG. 1D) Semi quantification data is showing significant increase in Col-V (top) and Kα1T (bottom) optical density when compared with stable.

(FIG. 2A) Presence of Collagen V (Col-V) and Kα1 Tubulin (Kα1T) in exosomes isolated from lung transplant recipients (LTxRs) diagnosed with bronchiolitis obliterans syndrome (BOS): Exosomes were isolated from plasma collected at 6 and 12 months of LTxRs diagnosed with BOS (n=21) and Stable (n=10). Western blot was performed to detect presence of Col-V. Immunoblot analysis of Col-V in exosomes from BOS LTxRs showed higher levels of Col-V in comparison to stable. (FIG. 2B) Semi-quantification by densitometry revealed significant increase in Col-V optical density in comparison to stable, 6 month ($1.79\pm0.59$ vs $0.49\pm0.27$, $p<0.0001$) and 12 month ($2.06\pm0.65$ vs $0.56\pm0.26$, $p<0.0001$). (FIG. 2C) Kα1T western blot analysis of exosomes from BOS LTxRs (n=21) demonstrated that higher levels of Kα1T in comparison to stable (n=10). (FIG. 2D) Densitometry analysis showed significantly increase in Kα1T optical density when compared with stable, 6 month ($1.20\pm0.55$ vs $0.56\pm0.34$, $p=0.0049$) and 12 month ($1.41\pm1.02$ vs $0.71\pm0.37$, $p=0.0348$).

(FIG. 3A) Exosomes are present 6 and 12 months prior to diagnosis of bronchiolitis obliterans syndrome (BOS) in validation cohort from a collaborating institution. Exosomes were isolated from plasma collected at 6 month and 12 month of lung transplant recipients (LTxRs) diagnosed with BOS (n=10) and stable (n=10). Shows presence of exosomes in plasma collected at 6 and 12 month of BOS LTxRs but not in stable. (FIG. 3B) Shows densitometry analysis data, exosomes isolated from BOS patients has higher amount of self-antigens, 6 month (Optical Density, Collagen V (Col-V) (top), $1.24\pm1.06$ vs $0.13\pm0.07$, $p<0.0001$; Kα1 Tubulin (Kα1T) (bottom) $0.80\pm0.64$ vs $0.18\pm0.07$, $p<0.0001$) and 12 months (Optical Density, Col-V, $1.18\pm1.02$ vs.$0.12\pm0.05$, $p<0.0001$; Kα1T $0.94\pm0.59$ vs $0.21\pm0.09$, $p<0.0001$).

(FIG. 4A) Validation of detection of exosomes isolated from a different center prior to diagnosis of bronchiolitis obliterans syndrome (BOS). Exosomes were isolated from plasma collected at 6 and 12 month of lung transplant recipients (LTxRs) diagnosed with BOS (n=10) and stable (n=10). Shows detection of lung self-antigens containing exosomes 6 and 12 month samples prior to BOS diagnosis but not in stable. (FIG. 4B) Shows semi quantification analysis of optical density of Collagen V (Col-V) (top) (6 month: $3.5\pm2.9$ vs $1.09\pm0.84$; $p=0.0116$, 12 month: $4.39\pm2.79$ vs $1.57\pm1.39$ $p=0.0089$) and Kα1 Tubulin (Kα1T) (bottom) (6 month: $2.00\pm0.52$ vs $0.080\pm0.37$; $p=0.0251$, 12 month: $2.48\pm1.92$ vs $0.98\pm0.19$ $p=0.0042$). Exosomes isolated from plasma of BOS had significantly higher levels of self-antigens in comparison to stable.

(FIG. 5A) Receiver operating curve (ROC) were calculated for circulating exosomes with lung self-antigen (SAg), Collagen V (Col-V), at two time points (6 and 12 months) in discovery cohort to determine optimum threshold values. Col-V levels at 6 months (_____) had an area under curve (AUC) AUC=0.99 and 12 month (- - -) (AUC=0.98). (FIG. 5B) ROC was calculated for circulating exosomes with lung SAg, Kα1 Tubulin (Kα1T), at two time points (6 and 12 months) in discovery cohort to determine optimum threshold values. Kα1T levels had an AUC at 6 months (0.81) and 12 month (0.74). (FIG. 5C) Validation Cohort; ROC were calculated for circulating exosomes with lung SAgs at two time points (6 and 12 months) for combined validation cohorts from both collaborating centers. Validation cohort revealed that Col-V levels at 6 months had AUC=0.87 and at 12 month (AUC=0.82) (black). KαlT levels at 6 months had an AUC=0.85 and 12 months (AUC=0.82) respectively (Red).

DETAILED DESCRIPTION

Figure 1A:
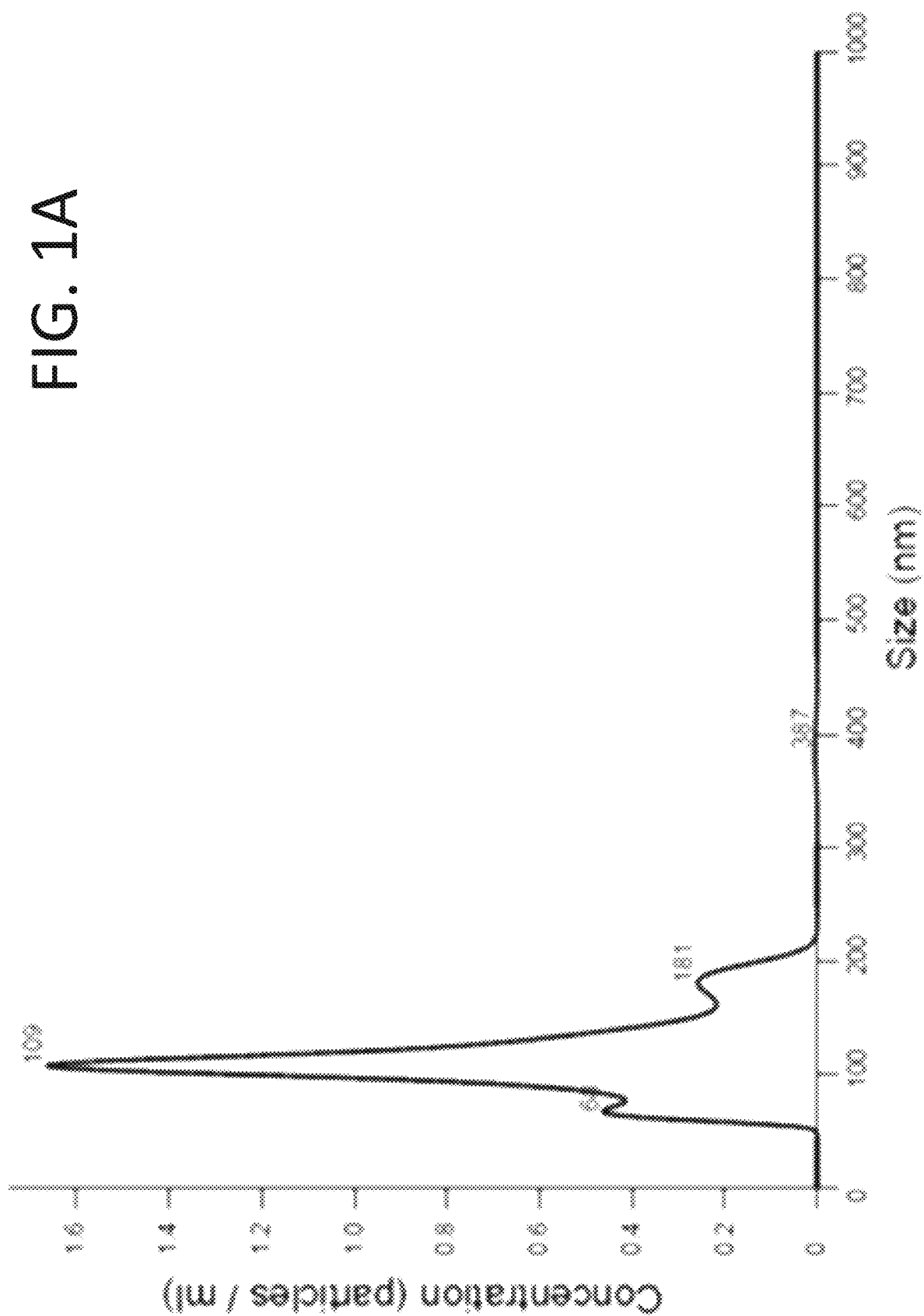
FIGS. 1A-1D.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, NY 2013); and Sambrook and Russel, Molecular Cloning: A Laboratory Manual 4th ed., Cold Spring Harbor Laboratory Press (Cold Spring Harbor, NY 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

One skilled in the art will recognize many methods and materials similar or equivalent to those described herein, which could be used in the practice of the present invention. Indeed, the present invention is in no way limited to the methods and materials described.

Some embodiments of the invention provide a method of diagnosing and treating chronic organ rejection in a subject. In some embodiments, the chronic organ rejection may comprise a rejection of single or bilateral allografted lungs. In other embodiments, the chronic organ rejection may comprise the rejection of any other organ, such as a solid organ (e.g., heart, kidney, etc.) or a liquid organ (e.g., bone marrow).

In some embodiments, the methods provided herein may include initially diagnosing chronic rejection. For example, in some aspects, chronic rejection may comprise the subject having and/or displaying symptoms of bronchiolitis obliterans syndrome (BOS). In some aspects, the subject may be undergoing BOS, but may not yet show or demonstrate any symptoms of BOS. Specifically, in some aspects, the subject may have BOS, but may not yet demonstrate any symptoms of BOS.

Moreover, in some embodiments, the methodologies contained herein can be employed to diagnose and treat BOS or other chronic organ rejection in advance of presentation of symptoms and/or worsening of the symptoms of chronic rejection (e.g., prior to chronic rejection or BOS requiring retransplantation to treat the subject when treatment can be affected using pharmaceutical agents). For example, the methodologies provided herein can be employed on a regular, semi-regular, or irregular basis to monitor the subject after receiving the allographic organ transplant. In particular, the methods contained herein can be employed on a daily, weekly, monthly, quadrennial, triennial, biannual, annual, etc. basis to assess a subject for early occurrence of chronic organ rejection. In some specific embodiments, the methods provided herein can be of sufficient selectivity and sensitivity to detect certain solid organ chronic rejection up to one year or more before the subject displays other clinical indicia of chronic rejection (e.g., BOS).

In some embodiments, the method of diagnosing and/or treating chronic organ rejection may include obtaining a sample from the subject (e.g., a subject that is not yet demonstrating any substantial symptoms of chronic organ rejection, such as BOS). For example, in some aspects, as provided herein, the sample may comprise any tissue from the subject. In particular, the sample may comprise a liquid sample from the subject, such as whole blood or blood components, such as plasma, serum, etc. In some embodiments, obtaining the sample (e.g., a liquid sample) and/or processing that sample to obtain the desired product (e.g., whole blood, plasma, serum, etc.) is well known in the art and employs methodologies known to those of skill in the art. In view of the aforementioned techniques, some aspects of the claimed methodologies can be considered to be relatively or substantially non-invasive (e.g., not required a sample of the organ that may be undergoing chronic rejection).

Some embodiments may include measurement of a marker contained within the sample. In some aspects, the marker may comprise one or more components of the structure of a transplanted organ. In some embodiments, the marker may comprise one or more self-antigens. For example, in some aspects and in the case of assessing chronic lung rejection (i.e., BOS), the marker may include a plurality of markers, such as Collagen-V and K-alpha 1 tubulin. In other aspects, such as in the case of chronic heart rejection, the markers may comprise myosin and vimentin and in the case of chronic kidney rejection, the markers may comprise fibronectin, Collagen-IV, and LG3. In other aspects, the one or more markers may include any other readily protein/glycoprotein that is readily discernable as a self-antigen from a transplanted organ. In yet other embodiments, the method may comprise assessing markers that are present as cell-free nucleic acid (cfDNA) that are detectable within the blood of the subject.

In some embodiments, the method may include the processing of the sample to obtain subunits thereof. For example, after isolation of the sample, the method may include isolating one or more components contained therein. In particular, the method may comprise processing the sample to obtain exosomes produced by the transplanted organ. In some aspect, this method of isolating exosomes may include techniques using ultracentrifugation and/or convention exosome-isolation kits provided by commercial organizations, like Invitrogen®. Specifically, in some aspects, the one or more markers of chronic organ rejection may be contained within the exosomes and/or displayed on or through the surface of the exosomes (i.e., as a transmembrane biomolecule).

Some embodiments provided herein may include diagnosing a subject (i.e., a subject that has received an allographic organ transplant) with chronic organ rejection (e.g., BOS). Moreover, in some aspects, the method may include diagnosing a subject that has not yet demonstrated any substantially discernable symptoms of chronic organ rejection, such as BOS.

In some embodiments, the method of diagnosing chronic organ rejection in the subject may include measuring the marker in the subject's sample. For example, as provided above, exosomes can be isolated from the subject's sample and the one or more markers can be measured in or on the exosomes. In some aspects, the expression of the one or more markers can be measured using the methodologies contained herein. Specifically, RNA or protein levels of the marker(s) can be measured using known techniques (e.g., RT-PCR or Western blotting), as provided herein.

Moreover, aspects provided herein include a comparison of the expression of the marker(s) in the subject's sample to a control (as defined herein). In view of this comparison, assessments/diagnoses regarding chronic rejection (e.g., BOS) can be made. For example, in the event that there is an increase in the expression of the marker(s) in subject's sample compared to the control, then the subject can be diagnosed as having chronic rejection. Conversely, if there is a decrease or no change in the expression of the marker(s) in the subject's sample compared to the control, then the subject can be either diagnosed as not having chronic rejection or having an indeterminate diagnosis such that additional monitoring should be undertaken.

Some embodiments may further provide for the treatment of diagnosed chronic organ rejection, such as BOS. For example, after assessing expression of the marker(s), one or more therapeutic methodologies can be employed to attempt to address the chronic organ rejection. In some aspects, the one or more treatment methodologies may comprise the use of increased dosing/administration of pharmaceuticals that the subject is currently receiving. For example, some or all allographic organ transplant recipients may regularly receive one or more pharmaceuticals that suppress the subject's immune system (i.e., immunosuppressants). As such, in some aspects, upon diagnosis of chronic organ rejection using the methods provided herein, a healthcare provider can (i) increase the dose of the immunosuppressant(s), (ii) increase the number of immunosuppressant dosages received in a given time period, and/or (iii) place the subject on additional immunosuppressant(s) or replace the existing immunosuppressant with a potentially more efficacious immunosuppressant. Some examples of immunosuppressants are cyclosporine, tacrolimus, mycophenolate mofetil, sirolimus, azathioprine, alemtuzumab, and one or more statins. In addition to, or in lieu of, any of the above therapeutic methodologies, the therapeutic methodology may also comprise retransplantation of the transplanted organs.

Generally, some embodiments of the present invention can be used to identify, quantify, detect, assess, isolate, and/or augment expression levels of one or more markers. A marker may be any molecular structure produced by a cell, expressed inside the cell, accessible on the cell surface, or secreted by the cell. A marker may be any protein, glycoprotein, carbohydrate, fatty acid, nucleic acid, catalytic site, or any combination of these such as an enzyme, glycoprotein, cell membrane, virus, a particular cell, or other uni- or multimolecular structure. In some embodiments, the marker may comprise a body released from one or more cells, such as an exosome. In some embodiments, the marker may be a part of or displayed via the exosome (e.g., on a surface of the exosome).

A marker may be represented by a sequence of a nucleic acid or any other molecules derived from the nucleic acid. Examples of such nucleic acids include miRNA, tRNA, siRNA, mRNA, cDNA, genomic DNA sequences, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection of the marker may encompass the detection and/or determination of a change in copy number (e.g., copy number of a gene or other forms of nucleic acid) or in the detection of one or more translocations.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frame shift mutations, single nucleotide polymorphisms (SNPs), inversions, translocations, heterochromatic insertions, and differentially methylated sequences relative to a reference gene, whether alone or in combination.

In some embodiments of the invention, the marker may comprise a plurality of markers. For example, the plurality of markers may include one or more molecules that are known to play a role in chronic rejection. In some aspects, the markers may comprise molecules such as Collagen-V, K-alpha 1 tubulin, fibronectin, Collagen-IV, myosin and vimentin and LG3. In some embodiments, the markers may comprise any other molecules known now or in the future known to function as self-antigens. In some embodiments, a combination of one or more of the above-described potential markers can be looked at in combination with other markers to provide therapeutic information for one skilled in the art in the context of one or more forms of chronic rejection, such as BOS.

An allele of a gene may or may not produce a functional protein; may produce a protein with altered function, localization, stability, dimerization, or protein-protein interaction; may have overexpression, under-expression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

Some embodiments of the invention may comprise the use of one or more methods of amplifying a nucleic acid-based starting material (i.e., a template). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications. In some embodiments, the first and/or the second reagents may comprise one or more oligonucleotides (e.g., primers) that can specifically bind to DNA, RNA, and/or cDNA to detect the presence and/or expression of nucleic acids that correspond to one of the markers using techniques such as PCR, qPCR, qRT-PCR, northern blot, ddPCR, etc.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTPs). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethyl-amino-phenylazo) benzoic acid ("Dabcyl"); 4-(4'-dimethyl-amino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in real time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may assume a circular or other two dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays. In some embodiments, the first and/or the second reagents may comprise one or more oligonucleotides (e.g., primers) that can specifically bind to DNA, RNA, and/or cDNA to detect the presence and/or expression of nucleic acids that correspond to one or more markers using techniques such as PCR, qPCR, qRT-PCR, northern blot, etc.

Some embodiments of the invention may include assessing, determining, quantifying, or altering the expression of a marker. As used herein expression encompasses any and all processes through which material derived from a nucleic acid template may be produced. Expression thus includes RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, small interfering RNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following non-limiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, or any other method of detecting a specific nucleic acid now known or yet to be disclosed. Other examples include any process of assessing expression that uses an antibody including the following non-limiting examples, flow cytometry, immunohistochemistry, ELISA, Western blot, and immunoaffinity chromatography. Antibodies may be monoclonal, polyclonal, or any antibody fragment including an Fab, $F(ab)_2$, Fv, scFv, phage display antibody, peptibody, multispecific ligand, or any other reagent with specific binding to a marker. Such methods also include direct methods used to assess protein expression including the following non-limiting examples: HPLC, mass spectrometry, protein microarray analysis, PAGE analysis, isoelectric focusing, 2-D gel electrophoresis, and enzymatic assays. In some embodiments, the first and/or the second reagents may comprise one or more antibodies that can specifically bind to protein to detect the presence and/or expression of proteins that correspond to the markers. For example, the first and second reagents in the protein context can be assessed using techniques such as immunohistochemistry, western blot analysis, flow cytometry, ELISA, and immunoaffinity chromatography. Samples from which expression may be detected include single cells, whole organs or any fraction of a whole organ, whether in vitro, ex vivo, in vivo, or post-mortem. Some samples from which expression may be detected also include blood, whole blood, serum, plasma, or fractions thereof, such as exosomes.

Other methods used to assess expression include the use of natural or artificial ligands capable of specifically binding one or more markers, including a protein, carbohydrate, fat, nucleic acid, catalytic site, or any combination of these such as an enzyme, glycoprotein, cell membrane, virus, cell, organ, organelle, or any uni- or multimolecular structure that constitutes a marker that may be specifically bound by a ligand. Such ligands include antibodies, antibody complexes, conjugates, natural ligands, small molecules, nanoparticles, or any other molecular entity capable of specific binding to a marker. Ligands may be associated with a label such as a radioactive isotope or chelate thereof, dye (fluorescent or non-fluorescent,) stain, enzyme, metal, or any other substance capable of aiding a machine or a human eye from differentiating a cell expressing a marker from a cell not expressing a marker.

Positive expression encompasses any difference between a cell expressing markers and a cell that does not express one or more of the markers. The exact nature of positive expression varies by the method, but is well known to those skilled in the art of practicing a particular method. Positive expression may be assessed by a detector, an instrument containing a detector, or by aided or unaided human eye. Examples include but are not limited to specific staining of cells expressing a target in an IHC slide, binding of RNA from a sample to a microarray and detection of binding through the use of said microarray, a particular rate of dye incorporation in real-time RTPCR measured in $\Delta Ct$ or alternatively in the number of PCR cycles necessary to reach a particular optical density at a wavelength at which a double stranded DNA binding dye (e.g. SYBR Green) incorporates, through release of label from a previously labeled reporter probe used in a real-time RTPCR reaction, detection of fluorescence on a cell expressing a target by a flow cytometer, the presence of radiolabeled bands on film in a Northern blot, detection of protein levels using a Western blot, detection of labeled blocked RNA by RNAse protection assay, cell death measured by apoptotic markers, cell death measured by shrinkage of a tumor, or any other signal for the expression of a marker in existence now or yet to be developed. In some aspects of the invention, positive expression is a sufficient level of expression to correlate with a particular diagnosis, such as chronic organ rejection, such as BOS.

In some aspects of the invention, reduced expression constitutes no detectable expression. However, the concept of reduced expression further encompasses insufficient expression to reach or exceed a threshold, cutoff, or level that has been previously shown to result in a particular cellular or physiological response. Reduced expression may include similar expression relative to a control that has been previously determined not to express the marker(s) or similar expression to a control that has been previously determined not to exhibit the response. In this case, even though expression may be detectable, it still constitutes reduced expression. In some aspects of the invention, an expression level of a marker in a control known to have a reduced or increase risk of recurrence is predetermined and expression similar to that level is correlated with reduced or increase risk of recurrence. Increased or reduced expression includes expression that is 75% 50%, 25%, 10%, 5%, 1%, 0.1%, greater or less of that of a control cell or a median level of expression in a population. Reduced expression may also include greater than or less than $1\times10^{-5}$ greater or less expression normalized to the expression of a housekeeping gene.

The invention contemplates assessing the expression of the marker(s) in any biological sample from which the expression may be assessed. One skilled in the art would know to select a particular biological sample (or just "sample") and how to collect said sample depending upon the marker that is being assessed. Examples of sources of samples include but are not limited to biopsy or other in vivo or ex vivo analysis of prostate, breast, skin, muscle, fascia, brain, endometrium, lung, head and neck, pancreas, small intestine, blood, plasma, serum, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. In one aspect of the invention, the sample comprises a non-invasive sample, such as a blood sample that can be used in its then-current state or processed for its components, such as plasma.

Assessing the risk of a particular disease outcome includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

The term "subject" is used in its broadest sense. In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing chronic organ rejection, including human patients that are suspected of having chronic organ rejection.

Some embodiments of the invention may include a method of comparing a marker in a sample relative to one or more control samples. A control may be any sample with a previously determined level of expression of the marker(s). A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The present invention further provides kits to be used in assessing the expression of a marker in a subject to assess the risk of developing disease, diagnosing the subject as having a stage of the disease, or determining to which stage the disease has progressed. Kits include any combination of components that facilitates the performance of an assay. A kit that facilitates assessing the expression of the markers may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu, reverse transcriptase, or other, and/or reagents that facilitate hybridization, as previously described. Kits according to the present invention may also include antibody-based reagents that can be used to detect the marker(s). For example, the kit can include one or more antibodies to detect the markers, a kit for exosome isolation, and/or any required reagents therefor (e.g., buffers, pre-poured acrylamide gels, etc.).

In some aspects of the invention, a probe may be affixed to a solid substrate. In other aspects of the invention, the sample may be affixed to a solid substrate. A probe or sample may be covalently bound to the substrate or it may be bound by some non-covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, attached or printed, either singly or in the formation of a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate in the case of a Southern Blot.

Some embodiments of the invention may include a therapeutic methodology to treat chronic organ rejection, such as BOS. The therapeutic methodology may include the administration of a pharmaceutical composition or a pharmacological composition to a subject that has been diagnosed with chronic organ rejection. Such pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed.

The concept of a pharmaceutical composition encompasses a compound or a pharmaceutically acceptable salt thereof with or without any other additive. The physical form of the invention may affect the route of administration and one skilled in the art would know to choose a route of administration that takes into consideration both the physical form of the compound and the disorder to be treated. Pharmaceutical compositions may be prepared using methodology well known in the pharmaceutical art.

In some aspects of the invention, the pharmaceutical composition can comprise one or more compounds or products that are capable of treating a subject with chronic organ rejection (e.g., the treatments considered by the medical community as the "standard of care" such as immunosuppressant(s)). In some embodiments, the pharmaceutical composition may comprise or include one or more compounds that are capable of affecting the immune system of the subject (e.g., immunosuppressant(s)) to reduce the chance of an immune system-mediated rejection of the allograph. The pharmaceutical composition may comprise one or more compounds that are capable of augmenting the immune system.

Moreover, in some embodiments, the method may include the administration of a combination of pharmaceutical compositions to subjects. Specifically, in some aspects, the combination may comprise the administration of a first pharmaceutical composition that and a second pharmaceutical composition that can affect different aspects of the immune system.

Pharmaceutical compositions include materials capable of modifying the physical form of a dosage unit. In one non-limiting example, the composition includes a material that forms a coating that contains the compound. Materials that may be used in a coating, include, for example, sugar, shellac, gelatin, or any other inert coating agent.

Pharmaceutical compositions including the disclosed agents may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or multi-phasic systems. In some embodiments, in the case of subject's diagnosis with BOS, the pharmaceuticals can be aerosolized so that the subject can inhale the immunosuppressant(s) to directly treat the chronic rejection of the lung transplant.

In some aspects of the invention, the pharmaceutical composition including the disclosed agents is in the form of a solvate. Such solvates are produced by the dissolution of the disclosed compound in a pharmaceutically acceptable solvent. Pharmaceutically acceptable solvents include any mixtures of one or more solvents. Such solvents may include pyridine, chloroform, propan-1-ol, ethyl oleate, ethyl lactate, ethylene oxide, water, ethanol, and any other solvent that delivers a sufficient quantity of the disclosed compound to treat the indicated condition.

Pharmaceutical compositions may also include at least one pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, and oils (including petroleum, animal, vegetable or synthetic oils.) Such carriers include particulates such as a tablet or powder, liquids such as oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers and formulations are well known in the art.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include the use of an inhaler or nebulizer, formulation with an aerosolizing agent, or via perfusion in a fluorocarbon or synthetic pulmonary surfactant. Compounds may be delivered in the context of a vesicle such as a liposome or any other natural or synthetic vesicle. Additional examples of suitable modes of administration are well known in the art.

A pharmaceutical composition formulated to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions may be prepared in a form that facilitates topical or transdermal administration. Such preparations may be in the form of a solution, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Determination of an effective and/or therapeutic amount of the disclosed agents is within the capability of those skilled in the art, especially in light of the detailed disclosure provided herein. The effective amount of a pharmaceutical composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the $IC_{50}$ (half maximal inhibitory concentration) of the pharmaceutical composition in cell lines or target molecules. Another example is the in vivo determination of the $LD_{50}$ (lethal dose causing death in 50% of the tested animals) of the pharmaceutical composition. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for administration also includes the determination of an effective therapeutic amount and a pharmaceutically acceptable dose, including the formulation of an effective dose range for use in vivo, including in humans.

Treatment of a condition or disease is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease. Generally, the effectiveness of treatment is determined by comparing treated groups with non-treated groups.

The addition of a therapeutically effective amount of a compound encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A dosing regimen including the regularity of and mode of administration will be dependent on any of a number of factors including but not limited to the subject being treated; the severity of the condition; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

The invention further encompasses kits that facilitate the administration of the disclosed compound to a diseased entity. An example of such a kit includes one or more unit dosages of one or more active ingredients. The unit dosage would be enclosed in a preferably sterile container and would be comprised of the compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage. In another aspect, the kit may include one or more additional compounds for administration and administration instructions therefor.

Embodiments of the present disclosure are further described in the following examples. The examples are merely illustrative and do not in any way limit the scope of the invention as claimed.

EXAMPLES

Methods
Sample Collection

Seventy-one lung transplant (LTx) recipients (LTxRs) were selected from collaborating institutions. This is a retrospective study based on prospectively collected plasma samples and clinical information. The inventors obtained institutional review board approval from all centers and consent from all subjects for this study. Among these patients, 41 were clinically diagnosed with BOS, 30 did not have BOS (control/stable group). For the discovery cohorts, 21 samples diagnosed with BOS and 10 stable (time matched control) were used. For the validation cohorts, serum from 20 BOS LTxRs and 20 stable/control LTxRs was collected at 6 and 12 months and at the time of BOS after LTx. All the plasma samples collected for LTxRs diagnosed as having BOS were time matched with plasma samples collected from the stable/control LTxRs.

Isolation of Exosomes

Circulating exosomes were isolated from plasma using ultracentrifugation method as described previously. To remove cell debris, plasma (1 ml) was centrifuged at 2000 g for 30 min then 10000 g for 40 min at 4° C. Supernatant was diluted with PBS and centrifuged at 100000 g for 120 mins at 4° C. However, when there was plasma less than 100 µl of sample, total exosomes isolation kit was used as described by manufacturer (Invitrogen) with minor modifications including passing through a 20 micron filter. The inventor's comparison of these two approaches provided similar results in Nanosight and lung self-antigen (Sag) measurements. Exosome pellet was suspended in PBS and concentration of total protein content of exosomes was analyzed using BCA method. All of the isolated exosomes were analyzed for size distribution and only those within the range (30-200 nm) were used for further analysis.

Size Distribution of Vesicles

Isolated exosomes were subjected to Nanosight NS300 instrument (Malvern Instruments, Amesbury, UK) to analyze size distribution of vesicles. The instrument is equipped with a syringe pump, a laser (488 nm) and a sensitive camera (sCMOS). Exosomes were diluted in PBS (1:50 dilution). Samples were captured and analyzed by applying constant flow rate (100). Video was captured at 30s with camera settings 14 and NTA 3.3 software was used to analyze the size of exosomes at detection threshold 7. All of the exosome samples used in this study had the range between 40-200 nm.

Western Blot Analysis

To analyze the presence of lung SAgs in exosomes, the inventor performed western blot analysis. Briefly, 10 μg of protein was used for SDS-PAGE electrophoresis and transferred to PVDF membrane. Primary Abs to SAgs anti-rabbit Collagen-V (Col-V) (Abcam) and anti-rabbit K-alpha 1 tubulin (KαlT) (Santa Cruz) IgG were used to detect protein. Goat anti-rabbit IgG conjugated with horseradish peroxidase was used as secondary Ab. Blot was developed using enhanced chemiluminescent immunoblot detection kit. J Image Software (NIH) used for densitometry of the signal band.

Receiver Operating Curve (ROC) Analysis

Results obtained for the fold change from the Western blot analysis for lung SAgs containing exosomes, ROC determination was performed by GraphPad Prism version 7 for Windows (GraphPad Software, La Jolla California USA). The cut off values were determined from the discovery cohort for lung SAgs with 21 patients with BOS and 10 stable control (time-matched control LTxRs) at 6 and 12 months prior to clinical diagnosis of BOS. The validation cohort was from 20 BOS LTxRs and 20 control LTxRs from two different collaborating centers (10 from each center) at 6 and 12 months before development of BOS after LTx.

Statistical Analysis

Optical density of exosome containing lung SAgs was quantitated using ImageJ software. The optical density of SAgs were normalized with exosome specific marker Alix and CD9 and expressed as mean±standard deviation. The relative OD values for SAgs between BOS and stable LTxRs were compared using unpaired and paired non-parametric Mann-Whitney test. The two-sided Wilcoxon rank-sum test was used to compare the normalized level of each antigen between patients diagnosed with chronic rejection and patients with stable/control condition at 6 and 12 months before transplant. Bonferroni correction was utilized to adjust for multiple comparisons, so significance level of 0.0125 was used for each test (two antigens and two time points). The same procedure was repeated for the validation data. GraphPad Prism version 7 for Windows (GraphPad Software, La Jolla California USA) was used to perform the analysis.

Results

Clinical Data of Patients

Lung-transplant recipient (LTxR) demographics, lung transplant (LTx) details, and laboratory data of the discovery cohort (n=31) were collected by review of patient charts. The endpoint of BOS was diagnosed according to standard International Society for Heart and Lung Transplantation guidelines. Patient demographics including age, gender, ethnicity, and underlying diagnosis were not significantly different between LTxRs diagnosed with BOS and stable (time matched controls) (Table 1).

TABLE 1

Discovery Studies: Demographic of LTx Recipients

| Characteristics | Stable (years) 2000-2015 | BOS (years) 2002-2015 |
|---|---|---|
| Number | 10 | 21 |
| Sex (N and %) | | |
| Male | 7 (70%) | 15 (71.4%) |
| Female | 3 (30%) | 6 (28.6%) |
| Age (Y) Mean ± SD | 53.8 ± 8.0 | 50.7 ± 14.1 |
| Ethnicity (N and %) | | |
| Caucasians | 10 (100%) | 21 (100%) |
| Black | 0 | 0 |
| Bilateral Transplant | 10 | 21 |
| Disease (N and %) | | |
| Cystic Fibrosis | 2 (10%) | 8 (31%) |
| IPF | 3 (50%) | 6 (28.6%) |
| COPD | 4 (30%) | 5 (23.8%) |
| BOS | 0 | 1 (4.8%) |
| Interstitial lung disease | 0 | 1 (4.8%) |
| MCTD | 1 (10%) | 0 |

Figure 1B:
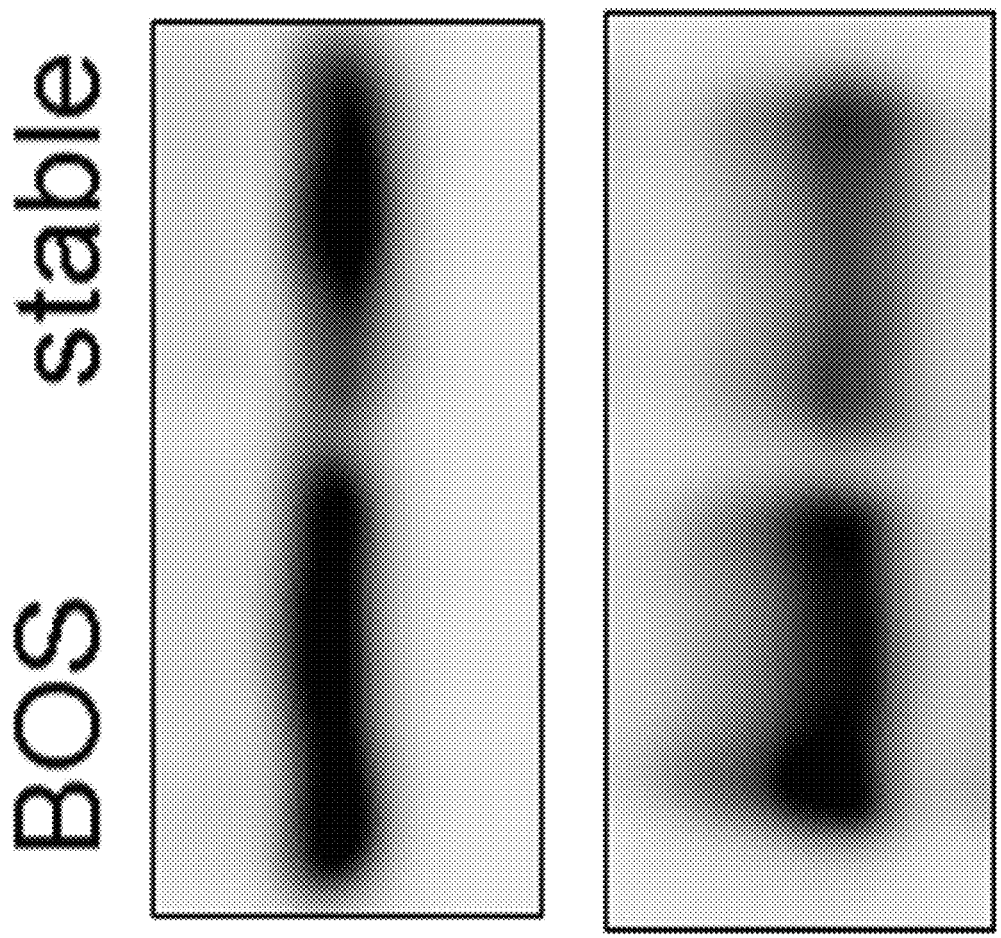

Definitions of abbreviations:
IPF: Idiopathic pulmonary fibrosis;
COPD: Chronic obstructive pulmonary disease;
BOS: Bronchiolitis obliterans syndrome;
MCTD: mixed connective tissue disease Size Distribution and Characterization of Exosomes Size distribution of isolated exosomes from LTxRs was carried out using Nanosight NS300 instrument. As shown in FIG. 1A, the vesicles size distribution used in this study ranged from 61-181 nm, compatible with exosomes as described in a position statement of the International Society for Extracellular Vesicles. Further, western blot analysis also showed the presence of Alix and CD9 exosomes markers in vesicles (FIG. 1B). These results confirm that the isolated vesicles are exosomes.

Figure 1C:
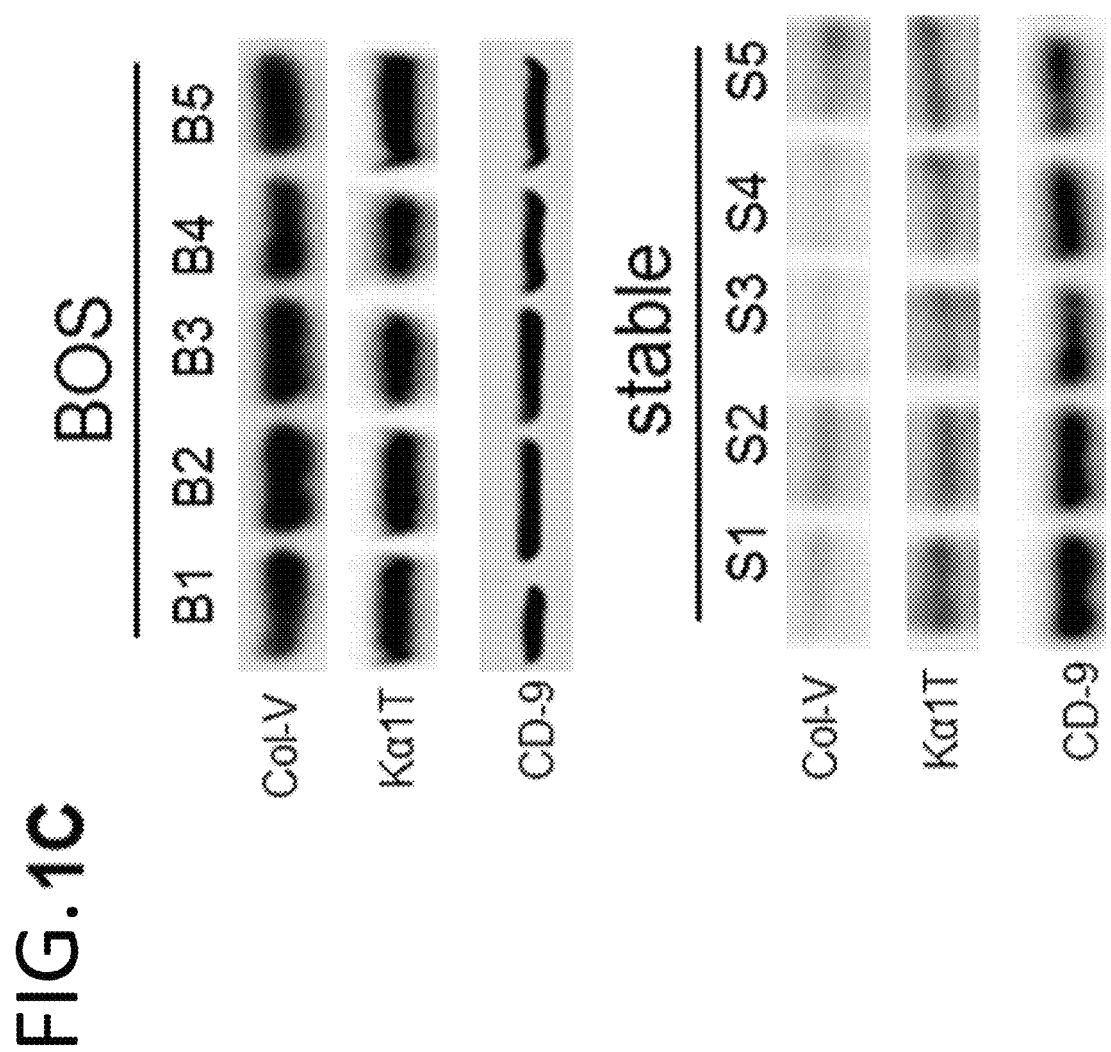
Figure 1D:
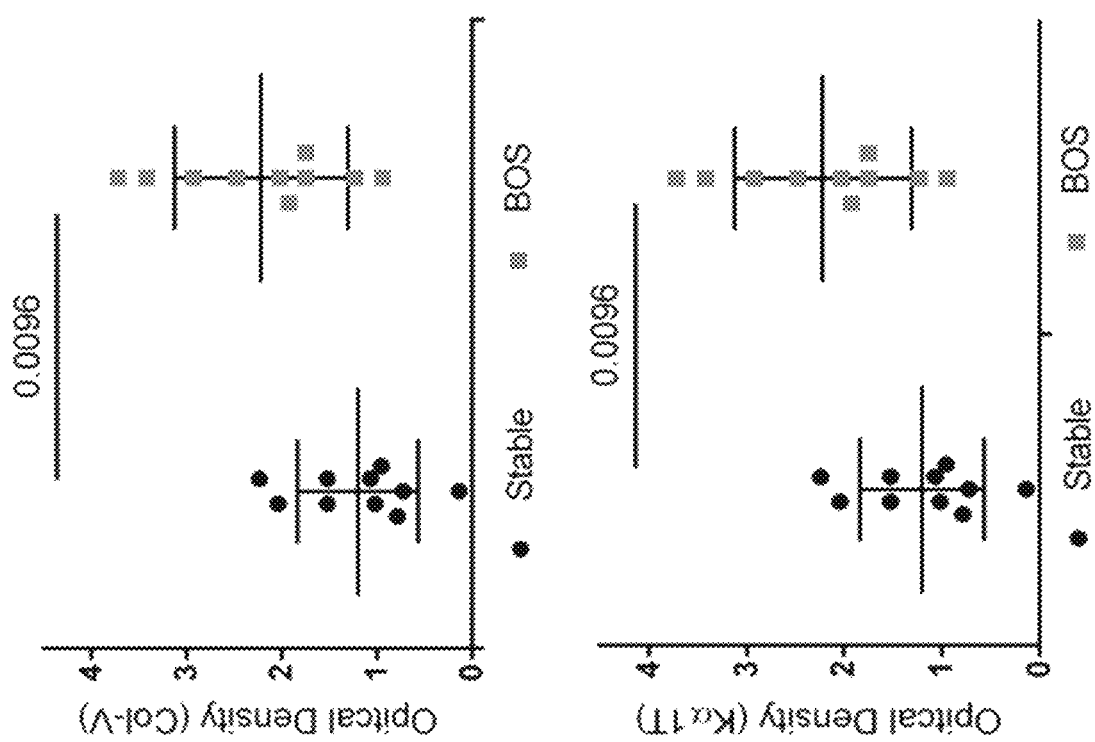

Increased Levels of Circulating Exosomes with Lung SAgs in LTxRs Diagnosed with BOS Previous studies from the inventor demonstrated that exosomes isolated from the LTxRs diagnosed with BOS contained lung SAgs (Col-V, KαlT). To confirm the inventor's earlier findings, the inventor isolated exosomes from plasma of LTxRs diagnosed with BOS from a different LTx center, and observed similar results (i.e., circulating exosomes from BOS LTxRs contained increased levels of Col-V (2.09±1.06 vs 1.17±0.66, p=0.0096; 1.79 fold) and KαlT (2.10±1.16vs1.19±0.67, p=0.0096; 1.76 fold)) in comparison to stable (time matched controls) (FIG. 1D). Western blot from 5 BOS subjects and 5 stable subjects are given in FIG. 1C. This result corroborates the inventor's previous findings.

Figure 2A:
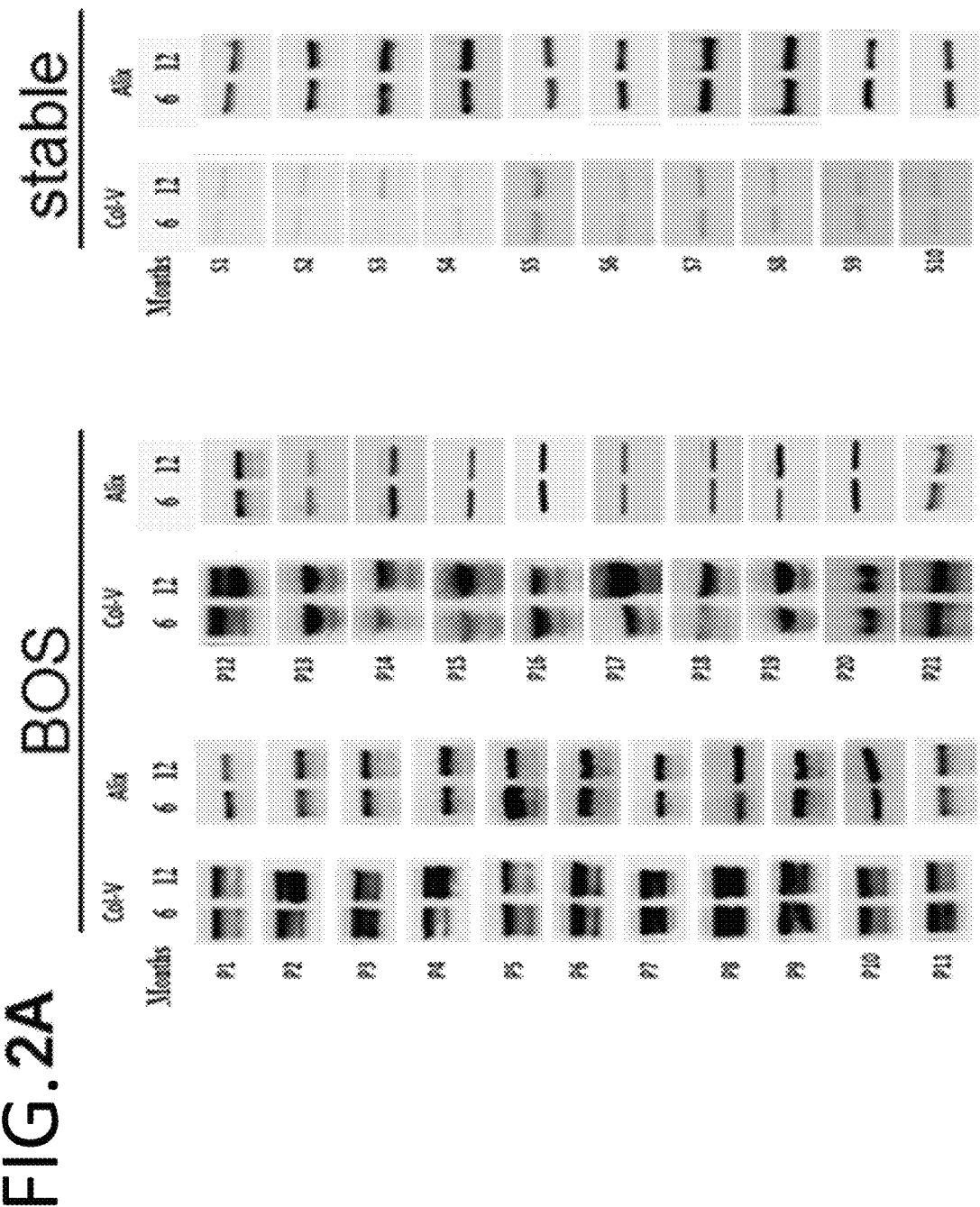
FIGS. 2A-2D.
Figure 2B:
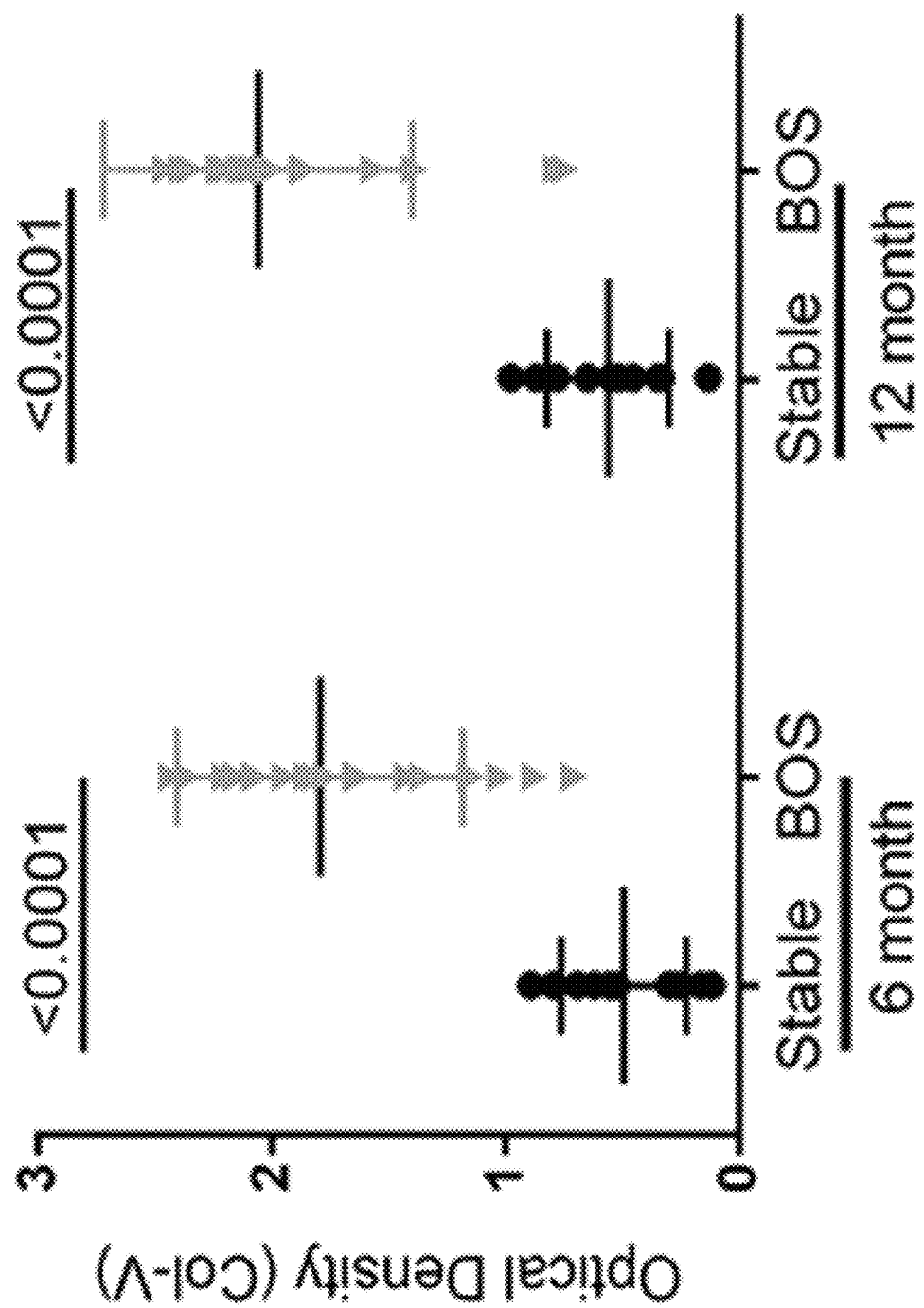

Detection of Circulating Exosomes with Lung SAg, Col-V, 12 Months Prior to the Diagnosis of BOS To determine whether circulating exosomes were detectable prior to the clinical diagnosis of BOS, the inventor isolated exosomes from plasma collected from 21 LTxRs with BOS and 10 stable (time matched control LTxRs) at 6 and 12 months prior to the diagnosis of BOS ("discovery cohort"). As shown in FIG. 2A and FIG. 2B, exosomes from LTxRs contained significantly higher levels of Col-V at 6 and 12 months prior to the diagnosis of BOS. Semi-quantitation by densitometry demonstrated significantly higher levels of lung SAgs at 6 months (1.79±0.59 vs 0.49±0.27, p<0.0001; 365 fold) and 12 months (2.06±0.65 vs 0.56±0.26, p<0.0001; 369 fold) in the exosomes isolated from LTxRs with BOS compared to matched stable (FIG.

Figure 2C:
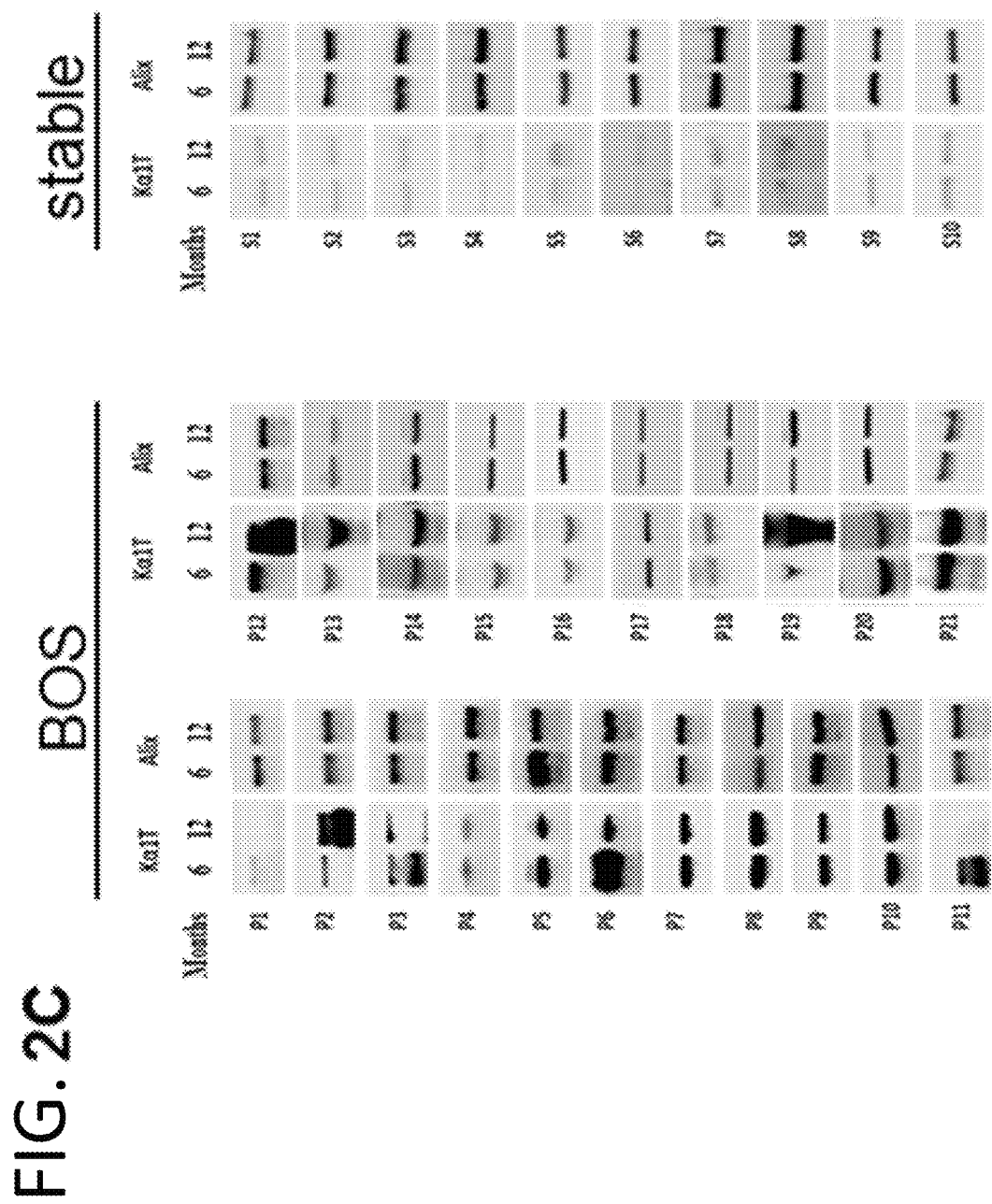
Figure 2D:
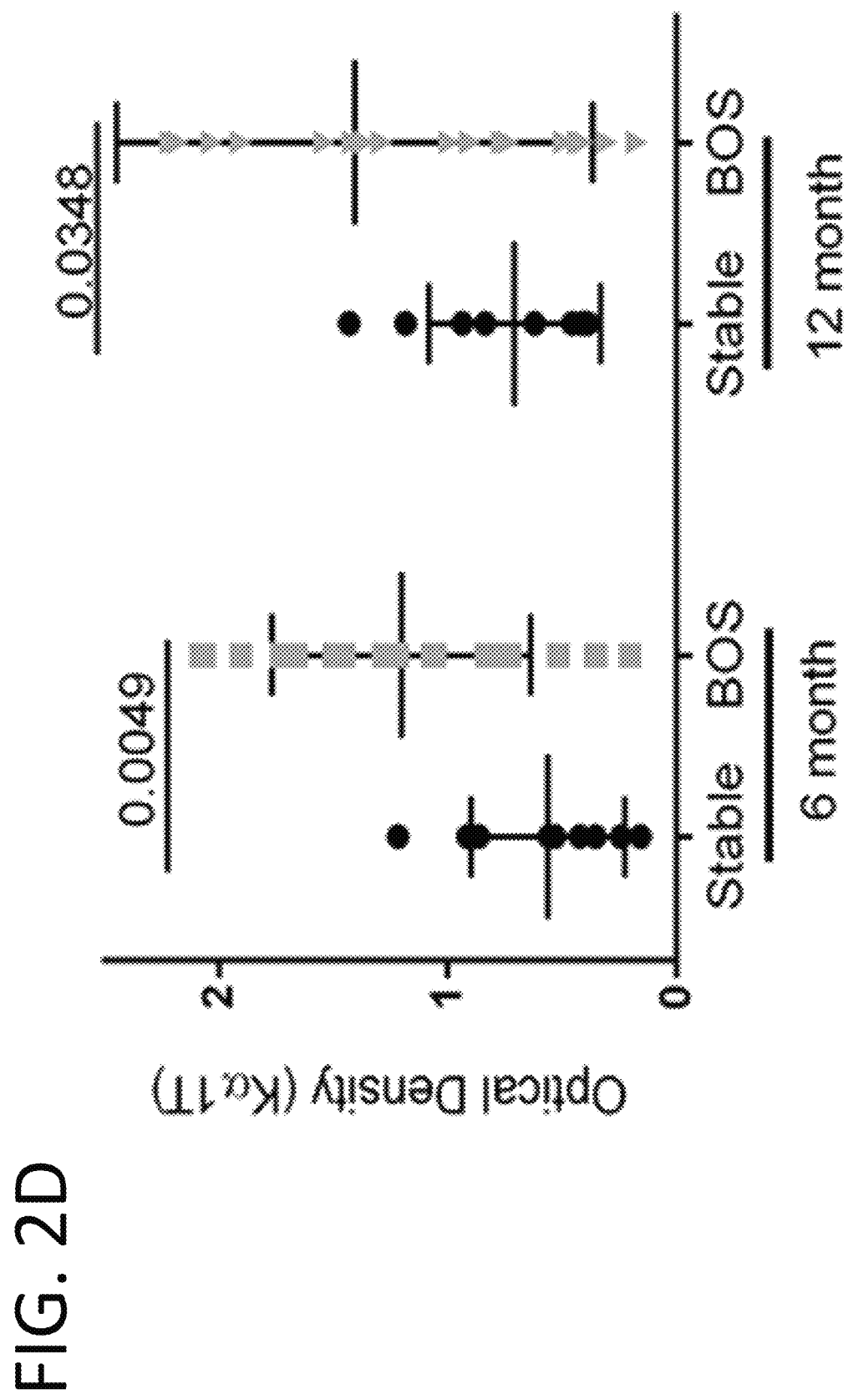

2B). The inventor also assessed the amount of KαlT in exosomes from the same patients' plasma using western blot. Results in FIG. 2C demonstrate that exosomes from LTxRs with BOS contained significantly increased levels of KαlT (FIG. 2C and FIG. 2D) compared to matched stable, both at 6 months (1.20±0.55 vs 0.56±0.34, p=0.0049; 2.14 fold) and 12 months (1.41±1.02 vs 0.71±0.37, p=0.0348; 1.99 fold) prior to the diagnosis of BOS. These results demonstrate that circulating exosomes containing significantly increased levels of both lung SAgs (KαlT, Col-V) are present in the circulation of LTxRs with BOS compared to stable (time matched controls) up to 12 months before the diagnosis of BOS.

Validation of Exosomes using Different Cohort of BOS Patients

Figure 3A:
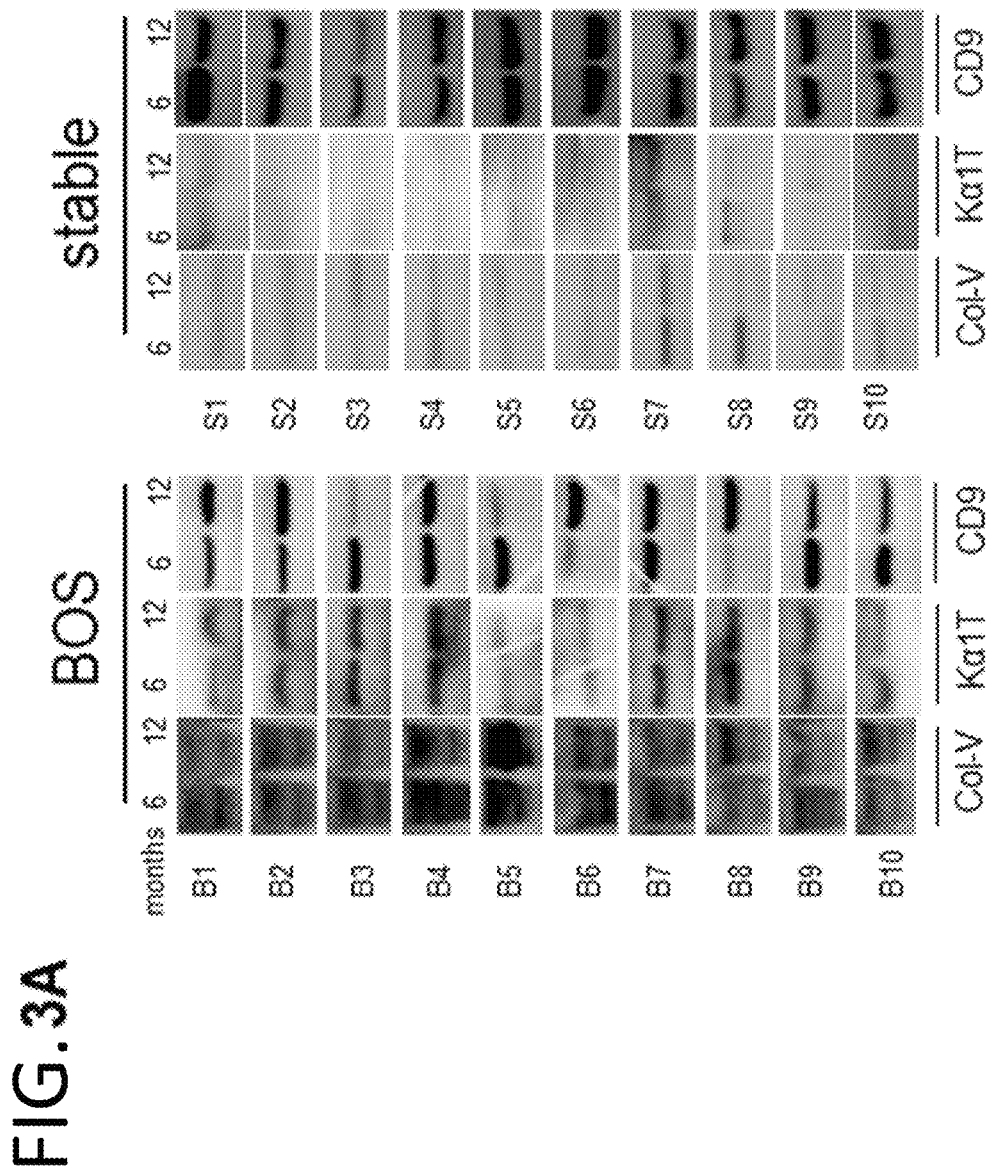
FIGS. 3A-3B.
Figure 3B:
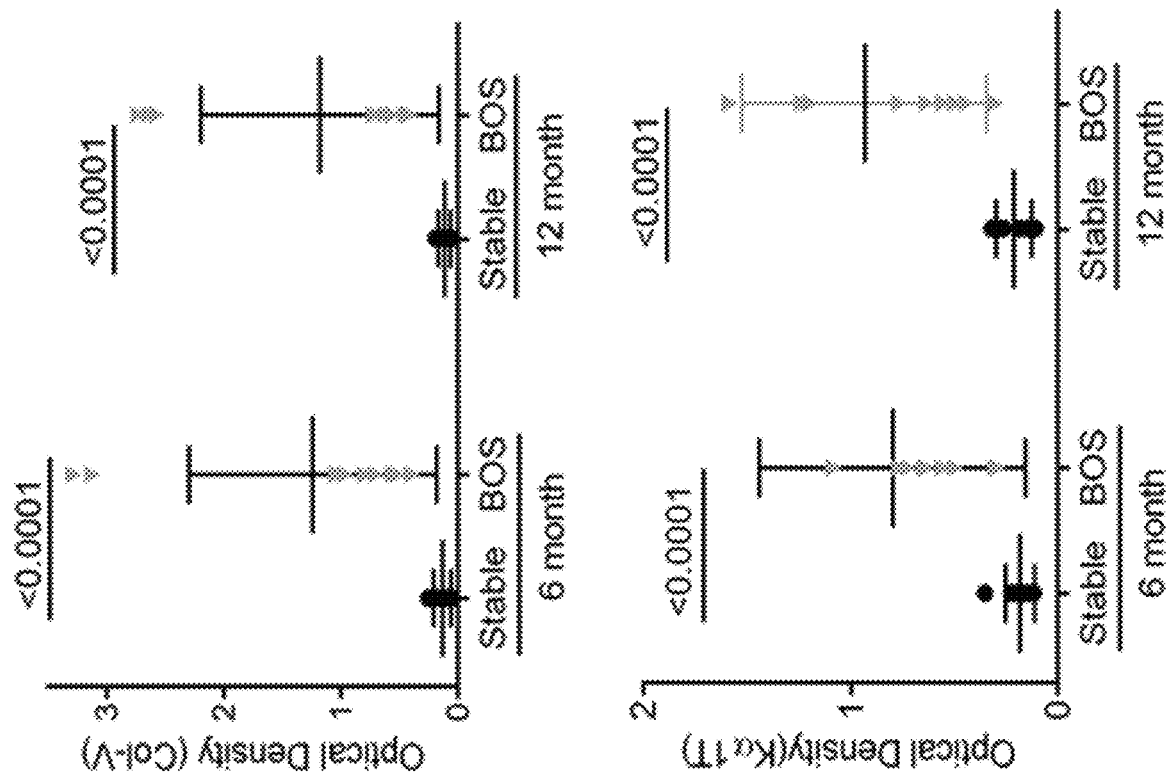

To validate the results obtained in the preliminary analysis indicating that circulating exosomes with increased levels of SAgs could identify patients at increased risk for BOS, the inventor analyzed circulating exosomes from independent cohorts of LTxRs consisting of 10 with BOS and 10 stable/control patients from a collaborating institution. Demographics of LTxRs used in this study are given in Table 2. Plasma collected at 6 and 12 months prior to the diagnosis of BOS and time-matched samples from matched stable LTxRs without BOS. In agreement with the inventor's preliminary results, exosomes isolated from BOS patients demonstrated significantly higher levels of lung SAgs compared with stable LTxRs (FIG. 3A and FIG. 3B).

TABLE 2

Validation Studies: Demographic of a Different Cohort of Lung Transplant Recipients from collaborating institutions

| Characteristics | Collaborator #1 samples | | Collaborator #2 Samples | |
| --- | --- | --- | --- | --- |
| | Stable (years) 2008-2013 | BOS (years) 2003-2013 | Stable (years) 2008-2012 | BOS (years) 2007-2012 |
| Number | 10 | 10 | 10 | 10 |
| Sex (N and %) | | | | |
| Male | 6 (60%) | 7 (70%) | 7 (70%) | 3 (30%) |
| Female | 4 (40%) | 3 (30%) | 3 (30%) | 7 (70%) |
| Age (Y) Mean ± SD | 51.3 ± 10.2 | 54.3 ± 15.4 | 53.8 ± 13.8 | 50.7 ± 11.3 |
| Ethnicity (N and %) | | | | |
| Caucasians | 8 (80%) | 10 (100%) | 9 (90%) | 9 (90%) |
| Black | 2 (20%) | 0 (0%) | 1 (10%) | 1 (10%) |
| Bilateral Transplant | 10 | 10 | 10 | 10 |
| Disease (N and %) | | | | |
| Cystic Fibrosis | 2 (20%) | 1 (10%) | 1 (10%) | 3 (30%) |
| IPF | 3 (30%) | 3 (30%) | 1 (10%) | 5 (50%) |
| COPD | 3 (30%) | 3 (30%) | 6 (60%) | 2 (20%) |
| Alpha 1 | 1 (10%) | 0 | 1 (10%) | 0 |
| Sarcoidosis | 0 | 2 (20%) | 0 | 0 |
| Scleroderma | 0 | 1 (10%) | 0 | 0 |
| PCH | 1 (10%) | 0 | 0 | 0 |
| Interstitial lung disease | 0 | 0 | 1 (10%) | 0 |

Definitions of abbreviations:
BOS: bronchiolitis obliterans syndrome;
COPD: Chronic obstructive pulmonary disease;
IPF: Idiopathic pulmonary fibrosis;
PCH: Pulmonary capillary hemangiomatosis Semi-quantitation by densitometry data (6 months, Col-V, 1.24±1.06 vs 0.13±0.07, 9.54 fold p<0.0001; KαlT 0.80±0.64 vs 0.18±0.07; 4.44 fold, p<0.0001) and 12 months (optical density, Col-V, 1.18±1.02 vs 0.12±0.05, p<0.0001 9.83 fold; KαlT 0.94±0.59 vs 0.21±0.09, p<0.0001, 4.48 fold) also corroborated western results.

Figure 4A:
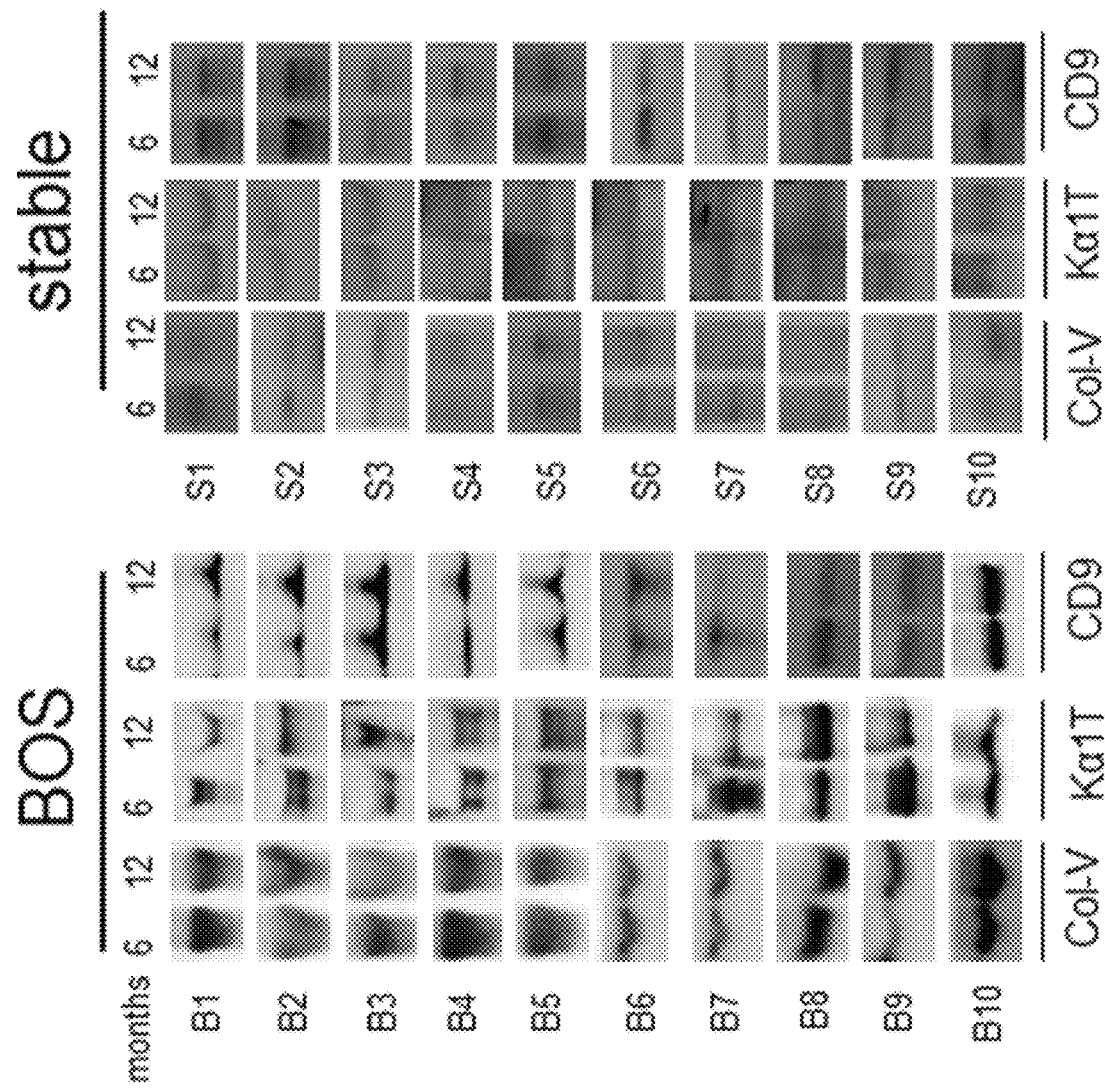
FIGS. 4A-4B.
Figure 4B:
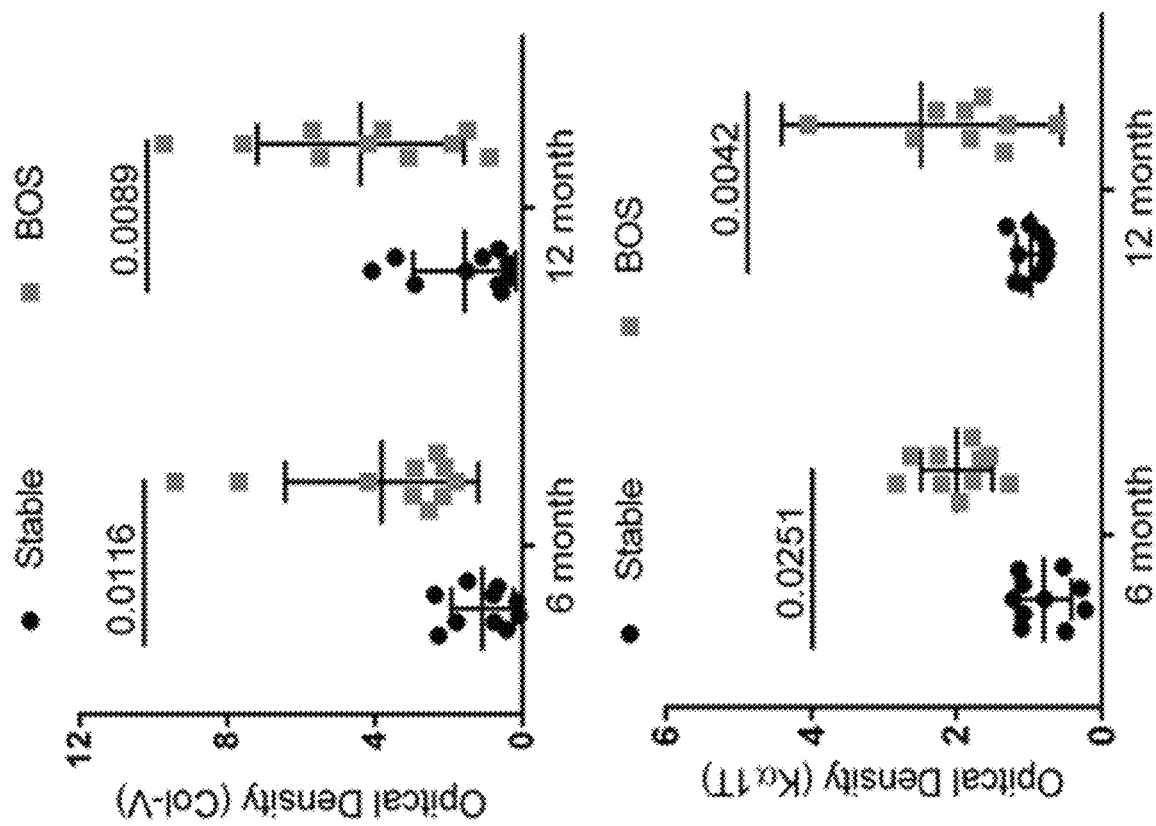

Further, to revalidate the findings, the inventor isolated circulating exosomes from plasma in 10 LTxRs with BOS and 10 stable (time matched controls) from a collaborating institution. Demographics of LTxRs used for this study from the collaborator are given in Table 2. Plasma was collected at 6 and 12 months before the diagnosis of BOS. The inventor observed similar results; the presence of exosomes containing lung SAgs 12 months prior to the diagnosis of BOS compared with stable 1 (FIG. 4A and FIG. 4B), Col-V (6 months: 3.5±2.9 vs 1.09±0.84; p=0.0116, 3.21 fold; 12 months: 4.39±2.79 vs 1.57±1.39, p=0.0089, 2.8 fold) and KαlT (6 months: 2.00±0.52 vs 0.080±0.37, p=0.025 1.25 fold; 12 months: 2.48±1.92 vs 0.98±0.19, p=0.0042, 2.53 fold). These results validate the initial results obtained in the discovery cohort using two separate set of LTxRs from two different centers, and provide evidence that circulating exosomes containing increased levels of lung SAgs can be detected in plasma up to 12 months before the diagnosis of BOS.

Sensitivity and Specificity Analysis

Figure 5A:
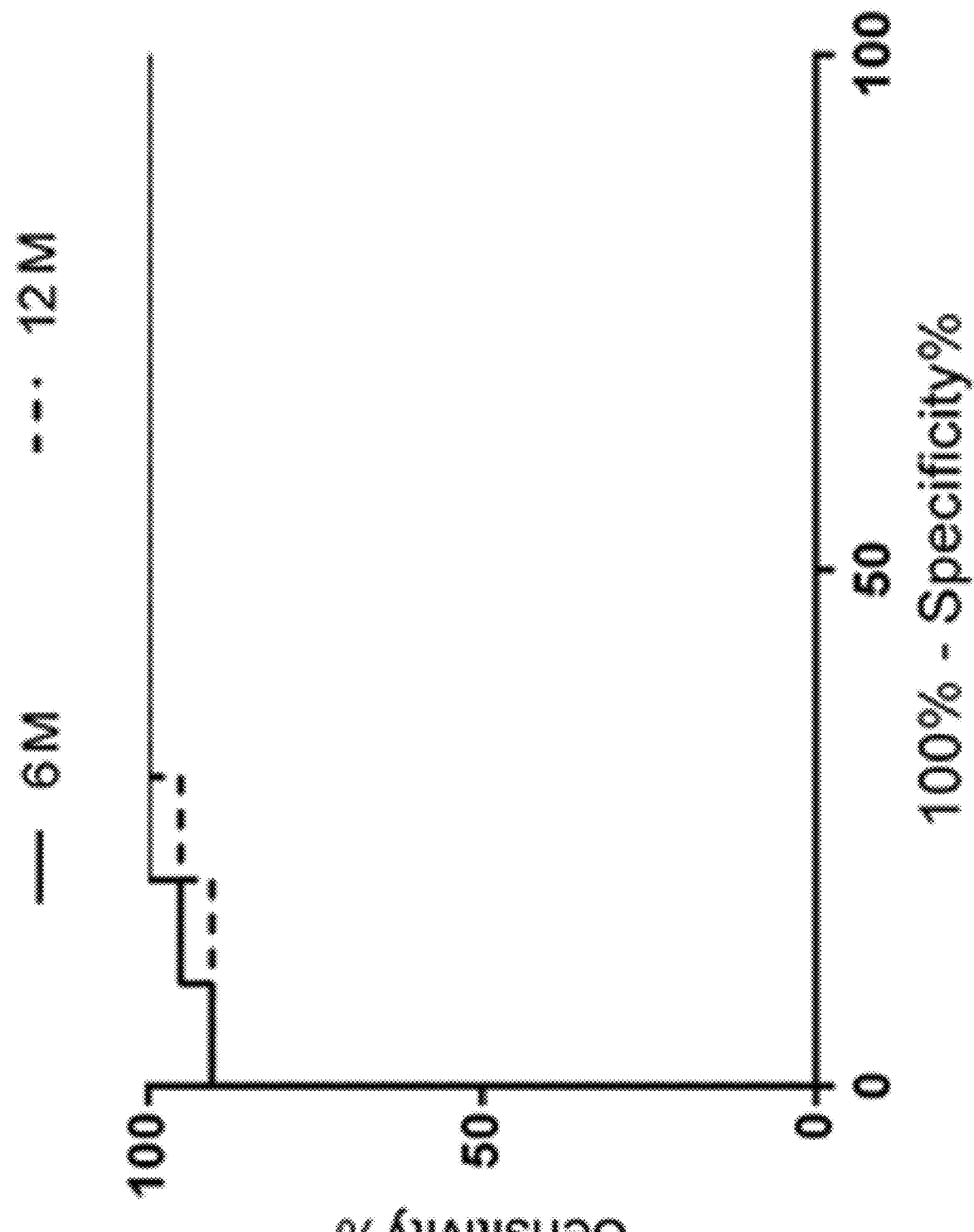
FIGS. 5A-5C.
Figure 5B:
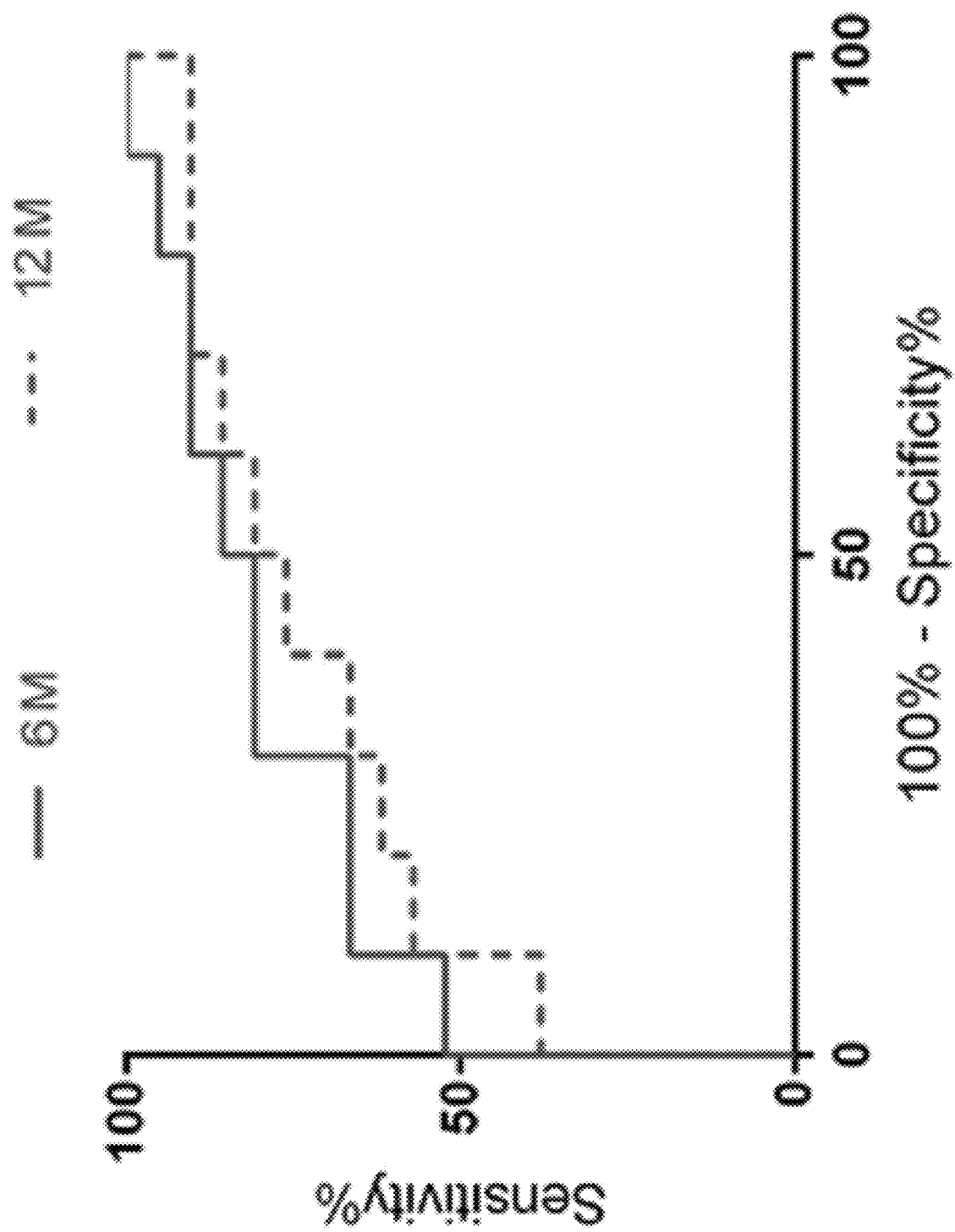
Figure 5C:
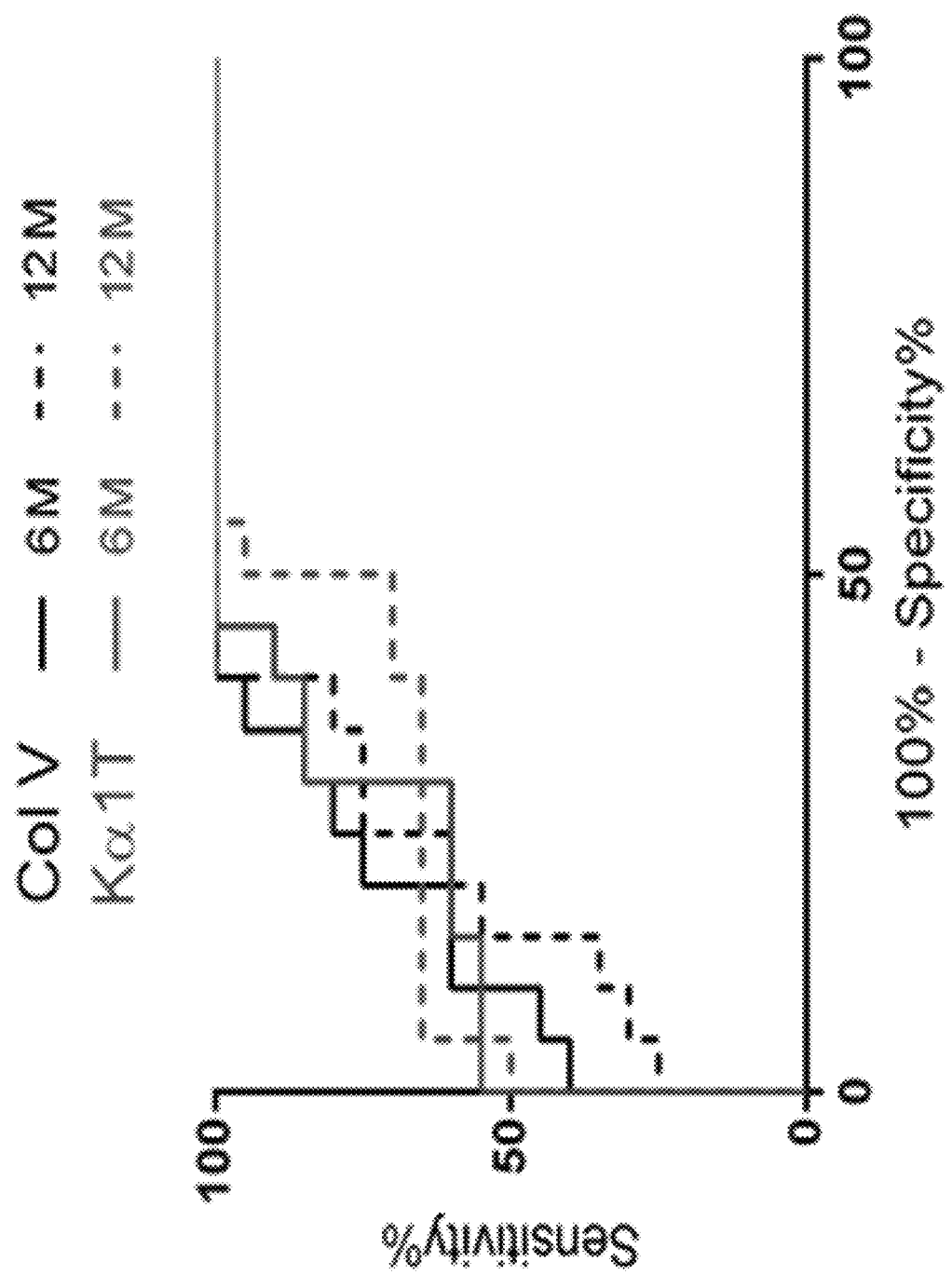

ROC analysis of lung SAgs (Col-V, KαlT) for the discovery cohort (FIG. 5A and FIG. 5B) and validation cohort (FIG. 5C) were performed at 6 and 12 month time points prior to BOS. In the discovery cohort, Col-V levels at 6 months had an area under curve (AUC) (AUC=0.99) and Col-V levels at 12 month had (AUC=0.98). KαlT levels had an AUC at 6 months (AUC=0.81) and 12 month (AUC=0.74) in discovery cohort respectively. Validation cohort revealed that Col-V levels at 6 months had AUC=0.87 and at 12 month (AUC=0.82). KαlT levels at 6 months had an AUC=0.85 and 12 months (AUC=0.82) respectively (Table 3).

ROC curve analysis using discovery cohort was used to determine the cut off values for sung SAgs (Col-V, KαlT) at two time points (6 and 12 months prior to BOS) (Table 3). In the discovery cohort, Col-V levels at 6 months (AUC=0.99) showed a sensitivity of 85.71% and a specificity of 100% at a cut off fold change of >1.09. Col-V levels at 12 months (AUC=0.98) showed a sensitivity of 90.48% and a specificity of 100% at a cut off fold change of >1.18. KαlT levels at 6 months (AUC=0.81) and 12 months (AUC=0.74) showed a sensitivity of 61.9% (6 months); 57.14% (12 months) and a specificity of 90% (6 months); 80% (12 months) at a cut off fold change of >1.06 for 6 months and >1.09 for 12 months respectively. The cutoff values for validation cohort was determined based on the discovery cohort. The validation cohort revealed that Col-V levels at 6 months (AUC=0.87) showed a sensitivity of 70% and a specificity of 80% at a cut off fold change of >0.99. Col-V levels at 12 months (AUC=0.82) showed a sensitivity of 60% and a specificity of 75% at a cut off fold change of >0.99. KαlT levels at 6 months (AUC=0.85) and 12 months (AUC=0.82) showed a sensitivity of 60% (6 months); 65% (12 months) and a specificity of 80% (6 months); 80% (12 months) at a cut off fold change of >1.07 for 6 months and >1.04 for 12 months respectively (Table 3).

TABLE 3

Statistical Analysis of Lung Self-Antigens for Discovery and Validation cohorts

| Lung SAgs | Time Points (months) | Discovery Cohort | | | | Validation Cohort | | | |
|---|---|---|---|---|---|---|---|---|---|
| | | AUC | Cut-off | Sensitivity (%) | Specificity (%) | AUC | Cut-Off | Sensitivity (%) | Specificity (%) |
| Col-V | 6 | 0.99 | >1.09 | 85.71 | 100 | 0.87 | >0.99 | 70 | 80 |
| | 12 | 0.98 | >1.18 | 90.48 | 100 | 0.82 | >0.99 | 60 | 75 |
| Kα1T | 6 | 0.81 | >1.06 | 61.9 | 90 | 0.85 | >1.07 | 60 | 80 |
| | 12 | 0.74 | >1.09 | 57.14 | 80 | 0.82 | >1.04 | 65 | 80 |

Definition of abbreviation:
AUC: area under curve;
SAgs: self-antigens;
Col-V: Collagen V;
Kα1T: Kα1 Tubulin Western blotting results obtained from both centers were analyzed in the validation cohort and their sensitivity and specificity were determined to predict elevated exosome lung SAgs in LTx population studied. The values obtained from the validation cohorts, though significant, were not similar to that obtained for the discovery cohort most likely due to smaller number of LTxRs analyzed for validation as well as potential differences in the diagnostic criterion between the two centers.

Discussion

Using a rigorous study design (discovery and validation cohorts) the inventor has demonstrated that circulating exosomes containing increased levels of lung SAgs (Kα1T, Col-V) are present, not only at the time of BOS diagnosis, but also preceding the diagnosis, and might, therefore, be useful for predicting the development of BOS in LTxRs. The inventor's results demonstrate that sera collected at 6 and 12 months, prior to the diagnosis of BOS, have significantly increased levels of circulating exosomes with lung SAgs. This may allow the development of strategies for prevention and early treatment of LTxRs who are at increased risk for developing BOS, an irreversible condition following LTx.

The inventor's team demonstrated that development of antibodies (Abs) to mismatched donor human leukocyte antigens as well as others have also demonstrated immune responses to lung SAgs (such as Collagen V) are strongly associated with the development of Primary graft dysfunction and BOS. In addition, primary graft dysfunction and respiratory viral infections are also widely recognized risk factors for BOS. Based on these, the inventor proposes that stress to the transplanted organs either by primary graft dysfunction, respiratory viral infections, or rejection episodes can release circulating exosomes with lung SAgs. Persistence of these exosomes in the circulation can lead to continued immune activation, increasing the risk of BOS. Therefore, circulating exosomes with lung SAgs could serve as a non-invasive biomarker for identifying LTxRs at risk for developing BOS. The inventor recently demonstrated the presence of lung SAgs in circulating exosomes isolated from LTxRs diagnosed with primary graft dysfunction, respiratory viral infections, acute rejection, and following de novo development of Abs specific to donor mismatched HLA. These exosomes also contain different immunoregulatory proteins such as transcription factors, adhesion molecules, co-stimulatory molecules and 20S proteasome which can elicit immune responses. Exosomes from LTxRs with BOS induced cellular and humoral immune responses to lung SAgs in mice immunized with exosomes in the absence of any adjuvants. Thus, the detection of increased lung SAgs-containing exosomes might serve as a non-invasive biomarker for graft injury, and their persistence may increase the likelihood for immune responses that ultimately result in chronic rejection.

During this study, the discovery cohort analysis of Col-V had a sensitivity of 85.7% and specificity of 100% at 6 months and 90.48% sensitivity and 100% specificity at 12 months prior to clinical diagnosis of BOS. For lung SAg, Kα1T, there was 61.9% sensitivity and 90% specificity at 6 months and sensitivity of 57% and specificity of 80% at 12 months. For the validation cohorts, levels of exosomes containing Col-V demonstrated sensitivity of 70% and specificity of 80% at 6 months and sensitivity of 60% with specificity of 75% at 12 months prior to clinical diagnosis of BOS. For lung SAg, Kα1T, sensitivity was 60% and specificity 80% at 6 months and 65% sensitivity and 80% specificity at 12 months. These results clearly demonstrate that determination of Col-V or Kα1T in circulating exosomes by western blot followed by semi-quantitation possesses higher positive predictive value with excellent sensitivity and specificity. Further, our data shows that circulating exosomes with lung SAgs can serve as a non-invasive biomarker in predicting risk for BOS at least 12 months prior to clinical diagnosis.

Previous reports from the inventor's team, and others, have demonstrated that plasma from heart transplant recipients diagnosed with cardiac allograft vasculopathy contain Abs to cardiac SAgs (myosin and vimentin). In addition, kidney transplant recipients diagnosed with transplant glomerulopathy, which is a known risk factor for developing chronic rejection, also develop Abs to kidney SAgs (fibronectin, Col-IV, and LG3). A recent publication from the inventor's group showed that exosomes isolated from heart and kidney transplant recipients contain tissue associated SAgs specific to the graft. Others have demonstrated the exosomes' importance in graft failure using a syngeneic murine heart transplant model, where administration of exosomes from sera of graft failure mice induced Abs to myosin and vimentin and caused graft loss in 8 days. A recent report demonstrated that circulating $C4d^+$ plasma endothelial macrovesicle levels were increased in human kidney transplant recipients related with acute rejection mediated by Ab development. This signifies that de novo development of Abs can stimulate exosome and may contribute in rejection. These results strongly suggest that there will also be development of circulating exosomes containing tissue restricted SAgs in other solid organ transplants and circulating exosomes with tissue associated SAgs can serve as a non-invasive biomarker for kidney and heart transplant recipients at risk for developing chronic rejection.

In conclusion, the inventor's findings demonstrate the importance of circulating exosomes in the development of immune responses leading to chronic rejection. This data, using different sets of plasma samples collected from 2 different LTx centers, demonstrates that circulating exosomes with lung SAgs can be detected 12 months prior to the diagnosis of BOS indicating that circulating exosomes with tissue restricted SAgs can be a viable non-invasive biomarker for identifying patients at risk for developing chronic rejection. Early detection of patients at risk for developing chronic rejection provides an opportunity to develop strategies to prevent or intervene prior to the onset of irreversible damage to the transplanted organ takes place. Further, based on the reports that Abs to tissue restricted SAgs can be detected prior to chronic rejection following human renal and cardiac transplantations, we propose that circulating exosomes with tissue associated SAgs has the potential to be a non-invasive biomarker for identifying not only LTxRs at risk for developing chronic rejection but also other solid organ transplant recipients at risk for developing chronic rejection, a major problem in clinical transplantation.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES

1. Estenne M, Hertz M I. Bronchiolitis obliterans after human lung transplantation. *Am J Resp Crit Care Med* 2003; 166 440-444.
2. Chambers D C, Yusen R D, Cherikh W S, Goldfarb S B, Kucheryavaya A Y, Khusch K, Lewey B J, Lund L H, Meiser B, Rossano J W, Stehlik J, International Society for H, Lung T. The Registry of the International Society for Heart and Lung Transplantation: Thirty-fourth Adult Lung And Heart-Lung Transplantation Report-2017; Focus Theme: Allograft ischemic time. *J Heart Lung Transplant* 2017; 36:1047-1059.
3. Pakhale S S, Hadjiliadis D, Howell D N, Palmer S M, Gutierrez C, Waddell T K, Chaparro C, Davis R D, Keshavjee S, Hutcheon M A, Singer L G. Upper lobe fibrosis: a novel manifestation of chronic allograft dysfunction in lung transplantation. *J Heart Lung Transplant* 2005; 24:1260-1268.
4. Sato M, Waddell T K, Wagnetz U, Roberts H C, Hwang D M, Haroon A, Wagnetz D, Chaparro C, Singer L G, Hutcheon M A, Keshavjee S. Restrictive allograft syndrome (RAS): a novel form of chronic lung allograft dysfunction. *J Heart Lung Transplant* 2011; 30:735-742.
5. Burke C M, Theodore J, Dawkins K D, Yousem S A, Blank N, Billingham M E, Van Kessel A, Jamieson S W, Oyer P E, Baldwin J C, et al. Post-transplant obliterative bronchiolitis and other late lung sequelae in human heart-lung transplantation. *Chest* 1984; 86:824-829.
6. Cooper J D, Billingham M, Egan T, Hertz M I, Higenbottam T, Lynch J, Mauer J, Paradis I, Patterson G A, Smith C. A working formulation for the standardization of nomenclature and for clinical staging of chronic dysfunction in lung allografts. International Society for Heart and Lung Translantation. *J Heart Lung Transplant* 1993; 12:713-716.
7. Estenne M, Maurer J R, Boehler A, Egan J J, Frost A, Hertz M I, Mallory G B, Snell G I, Yousem S. Bronchiolitis obliterans syndrome 2001: an update of the diagnostic criteria. *J Heart Lung Transplant* 2002; 21 297-310.
8. Kramer M R, Stoehr C, Whang J L, Berry G J, Sibley R, Marshall S E, Patterson G M, Starnes V A, Theodore J. The diagnosis of obliterative bronchiolitis after heart-lung and lung transplantation: low yield of transbronchial lung biopsy. *J Heart and Lung Transplantation* 1993; 12:675-681.
9. Hachem R R, Chakinala M M, Yusen R D, Lynch J P, Aloush A A, Patterson G A, Trulock E P. The predictive value of bronchiolitis obliterans syndrome stage 0-p. *Am J Respir Crit Care Med* 2004; 169:468-472.
10. Weigt S S, Wang, X., Palchevsky, V., Gregson, A. L., Patel, N., DerHovanessian, A., Shino, M. Y., Sayah, D. M., Birjandi, S., Lynch, J. P. 3rd, Saggar, R., Ardehali, A., Ross, D. J., Palmer, S. M., Elashoff, D., Belperio, J. A. Gene expression profiling of bronchoalveolar lavage cells preceding a clinical diagnosis of chronic lung allograft dysfunction. *PLoS One* 2017; 12:e0169894.
11. Kennedy V E, Todd J L, Palmer S M. Bronchoalveolar lavage as a tool to predict, diagnose and understand bronchiolitis obliterans syndrome. *Am J Transplant* 2013; 13:552-561.
12. Gunasekaran M, Xu, Z., Nayak, D. K., Sharma, M., Hachem, R, Walia, R., Bremner, R. M., Smith, M. A., Mohanakumar, T. Donor-derived exosomes with lung self-antigens in human lung allograft rejection. *Am J Transpl* 2017; 17(2):474-484.
13. Burlingham W J, Love R B, Jankowska-Gan E, Haynes L D, Xu Q, Bobadilla J L, Meyer K C, Hayney M S, Braun R K, Greenspan D S, Gopalakrishnan B, Cai J, Brand D D, Yoshida S, Cummings O W, Wilkes D S. IL-17-dependent cellular immunity to collagen type V predisposes to obliterative bronchiolitis in human lung transplants. *J Clin Invest* 2007; 117:3498-3506.
14. Gregson A L, Hoji, A., Injean, P., Poynter, S. T., Briones, C., Palchevskiy, V., Weigt, S. S., Shino, M X., Derhovanessian, A., Sayah, D., Saggar, R., Ross, D., Ardehali, A., Lynch, J. P. 3rd, Belperio, J. A. Altered exosomal RNA profiles in bronchoalveolar lavage from lung transplants with acute rejection. *Am J Resp Crit Care Med* 2015; 192:1490-1503.
15. Fisher C E, Kapnadak, S. G., Lease, E. D., Edelman, J. D., Limaye, A. P. Interrater agreement in the diagnosis of chronic lung allograft dysfunction after lung transplantation. *J Heart and Lung Transplantation* 2019; 38(3): 327-328.
16. Thery C, Witwer K W, Aikawa E, Alcaraz M J, Anderson J D, Andriantsitohaina R, Antoniou A, Arab T, Archer F, Atkin-Smith G K, Ayre D C, Bach J M, Bachurski D, Baharvand H, Balaj L, Baldacchino S, Bauer N N, Baxter A A, Bebawy M, Beckham C, Bedina Zavec A, Benmoussa A, Berardi A C, Bergese P, Bielska E, Blenkiron C, Bobis-Wozowicz S, Boilard E, Boireau W, Bongiovanni A, Borras F E, Bosch S, Boulanger C M, Breakefield X, Breglio A M, Brennan M A, Brigstock D R, Brisson A, Broekman M L, Bromberg J F, Bryl-Gorecka P, Buch S, Buck A H, Burger D, Busatto S, Buschmann D, Bussolati B, Buzas E I, Byrd J B, Camussi G, Carter D R, Caruso S, Chamley L W, Chang Y T, Chen C, Chen S, Cheng L, Chin A R, Clayton A, Clerici S P, Cocks A, Cocucci E, Coffey R I, Cordeiro-da-Silva A, Couch Y, Coumans F A, Coyle B, Crescitelli R, Criado M F, D'Souza-Schorey C, Das S, Datta Chaudhuri A, de Candia P, De Santana E F, De Wever O, Del Portillo H A, Demaret T, Deville S, Devitt A, Dhondt B, Di Vizio D, Dieterich L C, Dolo V, Dominguez Rubio A P, Dominici M, Dourado M R, Driedonks T A, Duarte F V, Duncan H M, Eichenberger R M, Ekstrom K, El Andaloussi S, Elie-Caille C, Erdbrugger U, Falcon-Perez J M, Fatima F, Fish J E, Flores-Bellver M, Forsonits A, Frelet-Barrand A, Fricke F, Fuhrmann G, Gabrielsson S, Gamez-Valero A, Gardiner C, Gartner K, Gaudin R, Gho Y S, Giebel B, Gilbert C, Gimona M, Giusti I, Goberdhan D C, Gorgens A, Gorski S M, Greening D W, Gross J C, Gualerzi A, Gupta G N, Gustafson D, Handberg A, Haraszti R A, Harrison P, Hegyesi H, Hendrix A, Hill A F, Hochberg F H, Hoffmann K F, Holder B, Holthofer H, Hosseinkhani B, Hu G, Huang Y, Huber V, Hunt S, Ibrahim A G, Ikezu T, Inal J M, Isin M, Ivanova A, Jackson H K, Jacobsen S, Jay S M, Jayachandran M, Jenster G, Jiang L, Johnson S M, Jones J C, Jong A, Jovanovic-Talisman T, Jung S, Kalluri R, Kano S I, Kaur S, Kawamura Y, Keller E T, Khamari D, Khomyakova E, Khvorova A, Kierulf P, Kim K P, Kislinger T, Klingeborn M, Klinke D J, 2nd, Kornek M, Kosanovic M M, Kovacs A F, Kramer-Albers E M, Krasemann S, Krause M, Kurochkin I V, Kusuma G D, Kuypers S, Laitinen S, Langevin S M, Languino L R, Lannigan J, Lasser C, Laurent L C, Lavieu G, Lazaro-Ibanez E, Le Lay S, Lee M S, Lee Y X F, Lemos D S, Lenassi M, Leszczynska A, Li I T, Liao K, Libregts S F, Ligeti E, Lim R, Lim S K, Line A, Linnemannstons K, Llorente A, Lombard C A, Lorenowicz M J, Lorincz A M, Lotvall J, Lovett J, Lowry M C, Loyer X, Lu Q, Lukomska B, Lunavat T R, Maas S L, Malhi H, Marcilla A, Mariani J, Mariscal J, Martens-Uzunova E S, Martin-Jaular L, Martinez M C, Martins V R, Mathieu M, Mathivanan S, Maugeri M, McGinnis L K, McVey M J, Meckes D G, Jr., Meehan K L, Mertens I, Minciacchi V R, Moller A, Moller Jorgensen M, Morales-Kastresana A, Morhayim J, Mullier F, Muraca M, Musante L, Mussack V, Muth D C, Myburgh K H, Najrana T, Nawaz M, Nazarenko I, Nejsum P, Neri C, Neri T, Nieuwland R, Nimrichter L, Nolan J P, Nolte-'t Hoen E N, Noren Hooten N, O'Driscoll L, O'Grady T, O'Loghlen A, Ochiya T, Olivier M, Ortiz A, Ortiz L A, Osteikoetxea X, Ostergaard O, Ostrowski M, Park J, Pegtel D M, Peinado H, Perut F, Pfaffl M W, Phinney D G, Pieters B C, Pink R C, Pisetsky D S, Pogge von Strandmann E, Polakovicova I, Poon I K, Powell B H, Prada I, Pulliam L, Quesenberry P, Radeghieri A, Raffai R L, Raimondo S, Rak J, Ramirez M I, Raposo G, Rayyan M S, Regev-Rudzki N, Ricklefs F L, Robbins P D, Roberts D D, Rodrigues S C, Rohde E, Rome S, Rouschop K M, Rughetti A, Russell A E, Saa P, Sahoo S, Salas-Huenuleo E, Sanchez C, Saugstad J A, Saul M J, Schiffelers R M, Schneider R, Schoyen T H, Scott A, Shahaj E, Sharma S, Shatnyeva O, Shekari F, Shelke G V, Shetty A K, Shiba K, Siljander P R, Silva A M, Skowronek A, Snyder O L, 2nd, Soares R P, Sodar B W, Soekmadji C, Sotillo J, Stahl P D, Stoorvogel W, Stott S L, Strasser E F, Swift S, Tahara H, Tewari M, Timms K, Tiwari S, Tixeira R, Tkach M, Toh W S, Tomasini R, Torrecilhas A C, Tosar J P, Toxavidis V, Urbanelli L, Vader P, van Balkom B W, van der Grein S G, Van Deun J, van Herwijnen M J, Van Keuren-Jensen K, van Niel G, van Royen M E, van Wijnen A J, Vasconcelos M H, Vechetti I J, Jr., Veit T D, Vella U, Velot E, Verweij F J, Vestad B, Vinas J L, Visnovitz T, Vukman K V, Wahlgren J, Watson D C, Wauben M H, Weaver A, Webber J P, Weber V, Wehman A M, Weiss D J, Welsh J A, Wendt S, Wheelock A M, Wiener Z, Witte L, Wolfram J, Xagorari A, Xander P, Xu J, Yan X, Yanez-Mo M, Yin H, Yuana Y, Zappulli V, Zarubova J, Zekas V, Zhang J Y, Zhao Z, Zheng L, Zheutlin A R, Zickler A M, Zimmermann P, Zivkovic A M, Zocco D, Zuba-Surma E K. Minimal information for studies of extracellular vesicles 2018 (MISEV2018): a position statement of the International Society for Extracellular Vesicles and update of the MISEV2014 guidelines. *J Extracell Vesicles* 2018; 7:1535750.

17. Sharma M, Ravichandran R, Bansal S, Bremner R M, Smith M A, Mohanakumar T. Tissue-associated self-antigens containing exosomes: Role in allograft rejection. *Hum Immunol* 2018; 79:653-658.

18. Zaffiri L, Shah R I, Stearman R S, Rothhaar K, Emtiazjoo A M, Yoshimoto M, Fisher A J, Mickler E A, Gartenhaus M D, Cohort L, Diamond J M, Geraci M W, Christie J D, Wilkes D S. Collagen type-V is a danger signal associated with primary graft dysfunction in lung transplantation. *Transpl Immunol* 2019; 56:101224.

19. Iwata T, Philipovskiy A, Fisher A J, Presson R G, Jr., Chiyo M, Lee J, Mickler E, Smith G N, Petrache I, Brand D B, Burlingham W J, Gopalakrishnan B, Greenspan D S, Christie J D, Wilkes D S. Anti-type V collagen humoral immunity in lung transplant primary graft dysfunction. *J Immunol* 2008; 181:5738-5747.

20. Kuo E, Maruyama T, Fernandez F, Mohanakumar T. Molecular mechanisms of chronic rejection following transplantation. *Immunol Res* 2005; 32:179-185.

21. Hachem R R, Tiriveedhi V, Patterson G A, Aloush A, Trulock E P, Mohanakumar T. Antibodies to K-alpha 1 tubulin and collagen V are associated with chronic rejection after lung transplantation. *Am J Transplant* 2012; 12:2164-2171.

22. Xu Z, Nayak, D., Yang, W., Baskaran, G., Ramachandran, S., Sarma, N., Aloush, A., Trulock, E., Hachem, R., Patterson, G. A., Mohanakumar, T. Dysregulated microRNA expression and chronic lung allograft rejection in recipients with antobidies to donor HLA. *Am J Transpl* 2015; 15:1933-1947.

23. Bharat A, Saini, D., Steward, N., Hachem, R., Trulock, E. P., Patterson, G. A., Meyers, B. F., Mohanakumar, T. Antibodies to self-antigens predispose to primary lung allograft dysfunction and chronic rejection. *Annals Thoracic Surgery* 2010; 90.

24. Bharat A, Kuo E, Saini D, Steward N, Hachem R, Trulock E P, Patterson G A, Meyers B F, Mohanakumar T. Respiratory virus-induced dysregulation of T-regulatory cells leads to chronic rejection. *Ann Thorac Surg* 2010; 90:1637-1644; discussion 1644.

25. Almaghrabi R S, Omrani, A. S., Memish, Z. A. Cytomegalovirus infection in lung transplant recipients. *Expert Rev Respir Med* 2017; 11:377-383.

26. Fisher C E, Mohanakumar, T., Limaye, A. P. Respiratory virus infections and chronic lung allograft dysfunction: Assessment of virology determinants. *J Heart and Lung Transplantation* 2016; 35:946-947.

27. Mohanakumar T, Sharma, M., Bansal, S., Ravichandran, R., Smith, M., Bremner, R. A novel mechanism for immune regulation after human lung transplantation. *J Thorac Cardiovasc Surg* 2019.

28. Gunasekaran M, Sharma M, Hachem R, Bremner R, Smith M A, Mohanakumar T. Circulating Exosomes with Distinct Properties during Chronic Lung Allograft Rejection. *J Immunol* 2018; 200:2535-2541.

29. Nath D S, Ilias Basha, H., Tiriveedhi, V., Alur, C., Phelan, D., Ewald, G. A., Moazami, N., Mohanakumar, T. Characterization of immune responses to cardiac self-antigens Myosin and Vimentin in human cardiac allograft recipients with antibody mediated rejection and cardiac allograft vasculopathy. *J Heart and Lung Transplantation* 2010; 29:1277-1285.

30. Mahesh B, Leong H S, Nair K S, McCormack A, Sarathchandra P, Rose M L. Autoimmunity to vimentin potentiates graft vasculopathy in murine cardiac allografts. *Transplantation* 2010; 90:4-13.

31. Angaswamy N, Klein C, Tiriveedhi V, Gaut J, Anwar S, Rossi A, Phelan D, Wellen J R, Shenoy S, Chapman W C, Mohanakumar T. Immune responses to collagen-IV and fibronectin in renal transplant recipients with transplant glomerulopathy. *Am J Transplant* 2014; 14:685-693.

32. Giral M, Foucher Y, Dufay A, Van Huyen J P, Renaudin K, Moreau A, Philippe A, Hegner B, Dechend R, Heidecke H, Brouard S, Cesbron A, Castagnet S, Devys A, Soulillou J P, Dragun D. Pretransplant sensitization against angiotensin II type 1 receptor is a risk factor for acute rejection and graft loss. *Am J Transplant* 2013; 13:2567-2576.
33. Gunasekaran M, Vachharajani N, Gaut J P, Maw T T, Delos Santos R, Shenoy S, Chapman W C, Wellen J, Mohanakumar T. Development of immune response to tissue-restricted self-antigens in simultaneous kidney-pancreas transplant recipients with acute rejection. *Clin Transplant* 2017; 31.
34. Banasik M, Boratynska M, Koscielska-Kasprzak K, Mazanowska O, Bartoszek D, Zabinska M, Myszka M, Nowakowska B, Halon A, Szyber P, Patrzalek D, Klinger M. Long-term follow-up of non-HLA and anti-HLA antibodies: incidence and importance in renal transplantation. *Transplant Proc* 2013; 45:1462-1465.
35. Sharma M, Liu W, Perincheri S, Gunasekaran M, Mohanakumar T. Exosomes expressing the self-antigens myosin and vimentin play an important role in syngeneic cardiac transplant rejection induced by antibodies to cardiac myosin. *Am J Transplant* 2018; 18:1626-1635.
36. Tower C M, Reyes, M., Nelson, K., Leca, N., Kieran, N., Muczynski, K., Jefferson, J. A., Blosser, C., Kukla, A., Maurer, D., Chandler, W., Najafian, B. Plasma C4d+ Endothelial Microvesicles Increase in Acute Antibody-Mediated Rejection. *Transplantation* 2017; 101:2235-2243.

What is claimed is:

1. A method of treating chronic organ rejection in a subject having previously received an allographic organ transplant, the method comprising:
    a) obtaining or having obtained a first plasma sample from the subject at a first time point, wherein the subject does not yet experience any symptom of chronic organ rejection;
    b) isolating from the first plasma sample one or more exosomes;
    c) measuring expression of K-alpha 1 tubulin (Ka1T) and Collagen-V (Col-V) within the one or more exosomes;
    d) repeating steps of a) through c) in a fixed cadence;
    e) obtaining or having obtained a last plasma sample from the subject, at a last time point about 6 months from the first time point;
    f) treating the subject with at least one therapeutic methodology when
        (i) Col-V AUC value is at least about 0.81; or
        (ii) Ka1T AUC value is at least about 0.82.

2. The method of claim 1, wherein the subject has previously received at least one of a lung transplant, a heart transplant, and a kidney transplant.

3. The method of claim 1, wherein the subject has previously received a lung transplant.

4. The method of claim 1, wherein the at least one therapeutic methodology comprises administration of at least one immunosuppressive agent.

5. The method of claim 4, wherein the subject is already receiving an immunosuppressive agent and the therapeutic methodology comprises administering an increased concentration of the immunosuppressive agent.

6. The method of claim 4, wherein the immunosuppressive agent is selected from the group consisting of cyclosporine, tacrolimus, mycophenolate mofetil, sirolimus, azathioprine, alemtuzumab, and one or more statins.

7. The method of claim 6, wherein immunosuppressive agent is aerosolized.

8. The method of claim 1, wherein the at least one therapeutic methodology comprises retransplantation of the allographed organ.

9. The method of claim 3, wherein the subject has previously received one of a single or a bilateral lung transplant.

10. The method of claim 1, wherein the chronic organ rejection comprises bronchiolitis obliterans syndrome (BOS).

* * * * *